US009186353B2

(12) United States Patent
Cowart et al.

(10) Patent No.: US 9,186,353 B2
(45) Date of Patent: Nov. 17, 2015

(54) TREATMENT OF OSTEOARTHRITIS PAIN

(75) Inventors: Marlon D. Cowart, Round Lake Beach, IL (US); Gin C. Hsieh, Long Grove, IL (US); Jorge D. Brioni, Vernon Hills, IL (US); James P. Sullivan, Deerfield, IL (US)

(73) Assignee: AbbVie Inc., North Chicago, IL (US)

( * ) Notice: Subject to any disclaimer, the term of this patent is extended or adjusted under 35 U.S.C. 154(b) by 365 days.

(21) Appl. No.: 12/767,608

(22) Filed: Apr. 26, 2010

(65) Prior Publication Data

US 2010/0273778 A1    Oct. 28, 2010

Related U.S. Application Data

(60) Provisional application No. 61/173,132, filed on Apr. 27, 2009, provisional application No. 61/173,161, filed on Apr. 27, 2009.

(51) Int. Cl.
| | |
|---|---|
| A61K 31/55 | (2006.01) |
| A61K 31/425 | (2006.01) |
| A61K 31/454 | (2006.01) |
| A61K 31/501 | (2006.01) |
| A61K 31/551 | (2006.01) |
| A61K 31/517 | (2006.01) |
| A61K 31/4375 | (2006.01) |
| A61K 31/40 | (2006.01) |
| A61K 31/497 | (2006.01) |
| A61K 31/445 | (2006.01) |
| A61K 31/428 | (2006.01) |
| A61K 31/395 | (2006.01) |
| A61K 31/41 | (2006.01) |

(52) U.S. Cl.
CPC ............. *A61K 31/428* (2013.01); *A61K 31/395* (2013.01); *A61K 31/40* (2013.01); *A61K 31/41* (2013.01); *A61K 31/425* (2013.01); *A61K 31/4375* (2013.01); *A61K 31/445* (2013.01); *A61K 31/454* (2013.01); *A61K 31/497* (2013.01); *A61K 31/501* (2013.01); *A61K 31/517* (2013.01); *A61K 31/551* (2013.01)

(58) Field of Classification Search
USPC .......... 514/217.01, 367, 322, 252.03, 252.06, 514/218, 266.22, 266.2, 300, 408, 253.01, 514/318, 254.1
See application file for complete search history.

(56) References Cited

U.S. PATENT DOCUMENTS

| | | | |
|---|---|---|---|
| 4,507,318 | A | 3/1985 | Cousse et al. |
| 5,086,054 | A | 2/1992 | Parish |
| 6,048,876 | A | 4/2000 | Annoura et al. |
| 6,166,023 | A | 12/2000 | Schindler et al. |
| 6,235,791 | B1 | 5/2001 | Breliere et al. |
| 6,515,013 | B2 | 2/2003 | Bennani et al. |
| 6,620,839 | B2 | 9/2003 | Bennani et al. |
| 6,838,466 | B2 | 1/2005 | Zhu et al. |
| 6,969,730 | B2 | 11/2005 | Cowart et al. |
| 7,094,790 | B2 | 8/2006 | Cowart et al. |
| 7,098,222 | B2 | 8/2006 | Altenbach et al. |
| 7,153,889 | B2 | 12/2006 | Altenbach et al. |
| 7,205,316 | B2 | 4/2007 | Altenbach et al. |
| 7,345,034 | B2 | 3/2008 | Zhao et al. |
| 7,358,263 | B2 | 4/2008 | Cowart et al. |
| 7,381,537 | B2 | 6/2008 | Demuth et al. |
| 7,462,599 | B2 | 12/2008 | Schilling et al. |
| 7,576,110 | B2 | 8/2009 | Cowart et al. |
| 7,696,193 | B2 | 4/2010 | Sehmi et al. |
| 7,732,162 | B2 | 6/2010 | Hoffman et al. |
| 7,799,773 | B2 | 9/2010 | Bamford et al. |
| 2002/0052383 | A1 | 5/2002 | Bakthavatchalam et al. |
| 2002/0138210 | A1 | 9/2002 | Wilkes et al. |
| 2002/0169188 | A1 | 11/2002 | Cowart et al. |
| 2003/0119796 | A1 | 6/2003 | Strony |
| 2004/0224954 | A1 | 11/2004 | Sattlegger et al. |
| 2004/0224980 | A1 | 11/2004 | Sattlegger et al. |
| 2005/0171181 | A1 | 8/2005 | Wager et al. |
| 2005/0182045 | A1 | 8/2005 | Nagase et al. |
| 2005/0245529 | A1 | 11/2005 | Stenkamp et al. |
| 2006/0007413 | A1 | 1/2006 | Nanba |
| 2006/0040918 | A1 | 2/2006 | Bamford et al. |
| 2006/0074103 | A1 | 4/2006 | Corte et al. |
| 2007/0066588 | A1 | 3/2007 | Cowart et al. |
| 2007/0066644 | A1 | 3/2007 | De Lera Ruiz et al. |
| 2007/0066821 | A1 | 3/2007 | Allison et al. |
| 2007/0078133 | A1 | 4/2007 | Liu et al. |
| 2007/0208005 | A1 | 9/2007 | Parr et al. |

(Continued)

FOREIGN PATENT DOCUMENTS

| | | |
|---|---|---|
| CA | 2734800 A1 | 2/2010 |
| DE | 10153345 A1 | 5/2003 |
| DE | 10153347 A1 | 5/2003 |
| EP | 188887 A1 | 7/1986 |
| EP | 251466 A2 | 1/1988 |

(Continued)

OTHER PUBLICATIONS

Boureau (The IPSO study, ibuprofen, paracetamol study in osteoarthritis. A randomized comparative clinical study comparing the efficacy and safety of ibuprofen and paracetamol analgesic treatment of osteoarthritis of theknee or hip, Ann Rheum dis. 2004; 63(9): pp. 1028-1034).*

(Continued)

*Primary Examiner* — Kathrien Cruz
(74) *Attorney, Agent, or Firm* — Lisa V. Mueller; Michael Best & Friedrich LLP

(57) ABSTRACT

This invention discloses a method of treatment of osteoarthritis pain by administration of a histamine $H_3$ receptor antagonist, described herein, a salt thereof, or a composition comprising such compound or salt.

4 Claims, No Drawings

(56) References Cited

U.S. PATENT DOCUMENTS

| | | |
|---|---|---|
| 2007/0299056 A1 | 12/2007 | Bamford et al. |
| 2008/0021081 A1 | 1/2008 | Liu et al. |
| 2008/0027041 A1 | 1/2008 | Hudkins et al. |
| 2008/0139589 A1 | 6/2008 | Kanatani et al. |
| 2008/0176925 A1 | 7/2008 | Butler et al. |
| 2008/0242653 A1 | 10/2008 | Liu et al. |
| 2008/0286810 A1 | 11/2008 | Demuth et al. |
| 2009/0036425 A1 | 2/2009 | Dow et al. |
| 2009/0068699 A1 | 3/2009 | Schilling et al. |
| 2009/0075938 A1 | 3/2009 | Wynne et al. |
| 2009/0076020 A1 | 3/2009 | Arnold et al. |
| 2009/0137587 A1 | 5/2009 | Naya et al. |
| 2009/0192168 A1 | 7/2009 | Muci et al. |
| 2010/0016344 A1 | 1/2010 | Wakefield et al. |
| 2010/0040575 A1 | 2/2010 | Hoffmann et al. |
| 2010/0204205 A1 | 8/2010 | Barak et al. |
| 2010/0216812 A1 | 8/2010 | Griffin |
| 2010/0227876 A1 | 9/2010 | Rech |
| 2010/0249144 A1 | 9/2010 | Demong et al. |
| 2010/0267714 A1 | 10/2010 | Jorgensen et al. |
| 2010/0273778 A1 | 10/2010 | Cowart et al. |
| 2010/0286160 A1 | 11/2010 | Gilbert et al. |
| 2010/0292188 A1 | 11/2010 | Denonne et al. |
| 2011/0009430 A1 | 1/2011 | Moran et al. |
| 2011/0098300 A1 | 4/2011 | Celanire et al. |
| 2011/0195932 A1 | 8/2011 | Wynne et al. |
| 2012/0071651 A1 | 3/2012 | Ku et al. |

FOREIGN PATENT DOCUMENTS

| | | |
|---|---|---|
| EP | 259977 A2 | 3/1988 |
| EP | 0668270 A2 | 8/1995 |
| EP | 0982300 | 3/2000 |
| EP | 1321169 A1 | 6/2003 |
| EP | 1595881 A1 | 11/2005 |
| EP | 1675578 A2 | 7/2006 |
| EP | 1961416 A1 | 8/2008 |
| EP | 2117540 A1 | 11/2009 |
| EP | 2195293 A2 | 6/2010 |
| EP | 2206496 A1 | 7/2010 |
| EP | 2238144 A1 | 10/2010 |
| EP | 2253615 A1 | 11/2010 |
| EP | 2289498 A1 | 3/2011 |
| EP | 2300426 A1 | 3/2011 |
| FR | 2856596 A1 | 12/2004 |
| GB | 1086191 A | 10/1967 |
| GB | 2210364 A | 6/1989 |
| JP | 2000047358 A | 2/2000 |
| JP | 2002236340 A | 8/2002 |
| JP | 2004131497 | 4/2004 |
| JP | 2005170934 A | 6/2005 |
| JP | 2005281223 A | 10/2005 |
| NL | 6412766 A | 5/1965 |
| WO | WO-9415928 A1 | 7/1994 |
| WO | WO-9520588 A1 | 8/1995 |
| WO | WO-0042023 A1 | 7/2000 |
| WO | WO-0044728 A1 | 8/2000 |
| WO | WO-0063208 A1 | 10/2000 |
| WO | WO-0064884 A1 | 11/2000 |
| WO | WO-0213821 A1 | 2/2002 |
| WO | WO-0244128 A2 | 6/2002 |
| WO | WO-02074758 A2 | 9/2002 |
| WO | WO-03066604 A2 | 8/2003 |
| WO | WO-03099276 A1 | 12/2003 |
| WO | WO-03104235 A1 | 12/2003 |
| WO | WO-2004026305 A1 | 4/2004 |
| WO | WO-2004035556 A1 | 4/2004 |
| WO | WO2004037801 A1 | 5/2004 |
| WO | WO-2004037813 A1 | 5/2004 |
| WO | WO-2004041776 A2 | 5/2004 |
| WO | WO-2004043458 A1 | 5/2004 |
| WO | WO-2004046110 A1 | 6/2004 |
| WO | WO2004056369 A1 | 7/2004 |
| WO | WO-2004098625 A2 | 11/2004 |
| WO | WO-2004099199 A1 | 11/2004 |
| WO | WO2004101546 A1 | 11/2004 |
| WO | WO-2005000315 A1 | 1/2005 |
| WO | WO-2005009471 A1 | 2/2005 |
| WO | WO-2005009976 A1 | 2/2005 |
| WO | WO2005018045 A1 | 2/2005 |
| WO | WO-2005032468 A2 | 4/2005 |
| WO | WO-2005058837 A1 | 6/2005 |
| WO | WO-2005072740 A2 | 8/2005 |
| WO | WO-2005080361 A1 | 9/2005 |
| WO | WO-2005087746 A1 | 9/2005 |
| WO | WO-2005103032 A2 | 11/2005 |
| WO | WO-2005108384 A1 | 11/2005 |
| WO | WO2005123723 A1 | 12/2005 |
| WO | WO-2006004937 A2 | 1/2006 |
| WO | WO2006018260 A1 | 2/2006 |
| WO | WO2006029906 A1 | 3/2006 |
| WO | WO-2006040192 A1 | 4/2006 |
| WO | WO2006061193 A1 | 6/2006 |
| WO | WO-2006072596 A1 | 7/2006 |
| WO | WO2006085692 A1 | 8/2006 |
| WO | WO-2006090142 A1 | 8/2006 |
| WO | WO2006097691 A1 | 9/2006 |
| WO | WO-2006103537 A2 | 10/2006 |
| WO | WO-2006103546 A2 | 10/2006 |
| WO | WO-2006090142 C2 | 11/2006 |
| WO | WO-2006123020 A1 | 11/2006 |
| WO | WO-2006124687 A1 | 11/2006 |
| WO | WO2006132424 A1 | 12/2006 |
| WO | WO2006132914 A2 | 12/2006 |
| WO | WO-2007003604 A2 | 1/2007 |
| WO | WO2007004735 A1 | 1/2007 |
| WO | WO2006132914 A3 | 3/2007 |
| WO | WO-2007024004 A1 | 3/2007 |
| WO | WO-2007025144 A1 | 3/2007 |
| WO | WO2007025596 A1 | 3/2007 |
| WO | WO-2007038074 A1 | 4/2007 |
| WO | WO-2007048595 A1 | 5/2007 |
| WO | WO2007052124 A1 | 5/2007 |
| WO | WO-2007126957 A2 | 11/2007 |
| WO | WO-2007137968 A1 | 12/2007 |
| WO | WO2007150010 A2 | 12/2007 |
| WO | WO-2008064310 A2 | 5/2008 |
| WO | WO-2008064317 A1 | 5/2008 |
| WO | WO-2008064318 A2 | 5/2008 |
| WO | WO-2008067257 A2 | 6/2008 |
| WO | WO2008104590 A2 | 9/2008 |
| WO | WO-2008151156 A1 | 12/2008 |
| WO | WO2009024823 A2 | 2/2009 |
| WO | WO2009030716 A1 | 3/2009 |
| WO | WO-2009039431 A2 | 3/2009 |
| WO | WO-2009081195 A1 | 7/2009 |
| WO | WO-2009085945 A1 | 7/2009 |
| WO | WO-2009092764 A1 | 7/2009 |
| WO | WO-2009100120 A2 | 8/2009 |
| WO | WO-2009100294 A2 | 8/2009 |
| WO | WO-2009115874 A1 | 9/2009 |
| WO | WO-2009124553 A2 | 10/2009 |
| WO | WO-2009147149 A1 | 12/2009 |
| WO | WO-2009151991 A1 | 12/2009 |
| WO | WO-2010007382 A1 | 1/2010 |
| WO | WO-2010071822 A1 | 6/2010 |
| WO | WO-2010080757 A2 | 7/2010 |
| WO | WO-2010129242 A2 | 11/2010 |
| WO | WO-2011083314 A1 | 7/2011 |
| WO | WO-2011083315 A1 | 7/2011 |
| WO | WO-2011083316 A1 | 7/2011 |

OTHER PUBLICATIONS

Berlin, et al., "Recent Advances in the Development of Histamine H3 Antagonists," Expert Opinion in Ther. Patents, 2007, vol. 17, pp. 675-687.
Collins, et al., "Emerging Therapies for Neuropathic Pain," Expert Opinion on Emerging Drugs, 2005, vol. 10 (1), pp. 95-108.
Cross, et al., "Rules for the Nomenclature of Organic Chemistry," 1976, Pure & Applied Chemistry, vol. 45 (1-8), pp. 13-30.
Dray, et al., "Future Targets to Control Osteoarthritis Pain," Arthritis Research and Therapy, 2007, vol. 9, 14 pages.

(56) References Cited

OTHER PUBLICATIONS

Dray, et al., "Pharmacology of Chronic Pain," Trends in Pharmacological Sciences, 1994, vol. 15 (6), pp. 190-197.
Dworkin, et al., "An Overview of Neuropathic Pain: Syndromes, Symptoms, Signs, and Several Mechanisms," Clinical Journal of Pain, 2002, vol. 18 (6), pp. 343-349.
Esbenshade, et al., "The Histamine H3 Receptor: An Attractive Target for the Treatment of Cognitive Disorders," British J. Pharm., 2008, vol. 154, pp. 1166-1181.
Fernihough, et al., "Pain Related Behaviour in Two Models of Osteoarthritis in the Rat Knee," Pain, 2004, vol. 112 (1/2), pp. 83-93.
Internaltional Search Report for Application No. PCT/US2010/032488, mailed on Nov. 2, 2010, 11 pages.
Annex to Form PCT/ISA/206 for Application No. PCT/US2010/032488, mailed Jun. 30, 2010, 7 pages.
Joshi, et al., "Animal Models of Pain for Drug Discovery," Expert Opinion on Drug Discovery, 2006, vol. 1, pp. 323-334.
Medhurst, et al., "Novel histamine $H_3$ receptor antagonists GSK189254 and GSK334429 are efficacious in surgically-induced and virally-induced rat models of neuropathic pain," Pain, 2008, vol. 138, pp. 61-69.
Medhurst, et al., "Structurally Novel Histamine H3 Receptor Antagonists GSK207040 and GSK334429 Improve Scopolamine-induced Memory Impairment and Capsaicin-Induced Secondary Allodynia in Rats," Biochemical Pharmacology, 2007, vol. 73, pp. 1182-1194.
Rubin, Bernard R., "Management of Osteoarthritic Knee Pain," Journal of the American Osteopathic Association, 2005, vol. 105, pp. S23-S28.
Sander, et al., "Histamine H3 Receptor Antagonists go to Clinics," Biol. Pharm. Bull., 2008, vol. 31, pp. 2163-2181.
Smith, et al., "Neuropathic Pain and the Electrophysiology and Pharmacology of Nerve Injury," Drug Develop. Research, 2001, vol. 54 (3), pp. 140-153.
Vinik, et al., "Diabetic Neuropathies," Medical Clinics of North America, 2004, vol. 88 (4), pp. 947-999.
Witkin, et al., "Selective Histamine H3 Receptor Antagonists for the Treatment of Cognitive Deficiencies and Other Disorders of the Central Nervous System," Pharmacology and Therapeutics, 2004, vol. 103, pp. 1-20.
Furniss, et al., "Vogel's Textbook of Practical Organic Chemistry," $5^{th}$ edition (1989), Longman Scientific & Technical, Essex CM20 2JE, England, Table of Contents.
Prescott, Ed., Methods in Cell Biology, vol. XIV, Academic Press, New York, N.Y., (1976), p. 33 et seq.
Airaksinen M.S., et al., "Histamine Neurons in Human Hypothalamus: Anatomy in Normal and Alzheimer Diseased Brains," Neuroscience, 1991, vol. 44 (2), pp. 465-481.
Arrang J.M., et al., "Auto-inhibition of Brain Histamine Release Mediated by a Novel Class ($H_3$) of Histamine Receptor," Nature, 1983, vol. 302, pp. 832-837.
Arrang J.M., et al., "Highly Potent and Selective Ligands for Histamine $H_3$-Receptors," Nature, 1987, vol. 327, pp. 117-123.
Arrang J.M., et al., "Histamine $H_3$ Receptor Binding Sites in Rat Brain Membranes:Modulations by Guanine Nucleotides and Divalent Cations," European Journal of Pharmacology, 1990, vol. 188, pp. 219-227.
Barbier A.J., et al., "Acute Wake-Promoting Actions of JNJ-5207852, a Novel, Diamine-based $H_3$ Antagonist," British Journal of Pharmacology, 2004, vol. 143, pp. 649-661.
Barbier A.J., et al., "Histaminergic Control of Sleep-Wake Cycles: Recent Therapeutic Advances for Sleep and Wake Disorders ," CNS and Neurological Disorders-Drug Targets, 2007, vol. 6, pp. 31-43.
Berlin M., et al., "Histamine H3 Receptor as a Drug Discovery Target," Journal of Medicinal Chemistry, 2011, vol. 54 (1), pp. 26-53.
Bernaerts P., et al., "Histamine H3 Antagonist Thioperamide Dose-Dependently Enhances Memory Consolidation and Reverse Amnesia Induced by Dizocilpine or Scopolamine in a One-Trail Inhibitory Avoidance Task in Mice," Behavioural Brain Research, 2004, vol. 154, pp. 211-219.

Bjenning C., et al., "Peripherally Administered Ciproxifan Elevates Hypothalamic Histamine Levels and Potently Reduces Food Intake in the Sprague Dawley Rat" in: Histamine Research in the New Mellennium, Watanabe T., et al., eds., Elsevier Science, 2001, pp. 449-450.
Blandina P., et al., "Histamine Neuronal System as a Therapeutic Target for the Treatment of Cognitive Disorders," Future Neurology, 2010, vol. 5 (4), pp. 543-555.
Bomann M.D., et al., "A Mild, Pyridine-Borane-Based Reductive Amination Protocol ," Journal of Organic Chemistry, 1995, vol. 60, pp. 5995-5996.
Brady W.T., et al., "Halogenated Ketenes. V. Cycloadditions of Dichloroketene to Olefins," Journal of Organic Chemistry, 1967, vol. 32, pp. 3703-3705.
Browman K.E. et al., "Enhancement of Prepulse Inhibition of Startle in Mice by the H3 Receptor Antagonists Thioperamide and Ciproxifan," Behavioural Brain Research, 2004, vol. 153 (1), pp. 69-76.
Burger A., et al., "2-(4-imidazolyl)cyclopropylamine ," Journal of Medicinal Chemistry, 1970, vol. 13, pp. 33-35.
Celanire S., et al., "Keynote Review: Histamine H3 Receptor Antagonists Reach Out for the Clinic," Drug Discovery Today, 2005, vol. 10 (23/24), pp. 1613-1627.
Charette A.B. et al., "(2S,3S)-(+)-(3-Phenylcyclopropyl)Methanol ," Org Syntheses Coll, 1999, vol. 76, pp. 86-96.
Chen Z., et al., "Effects of Histamine on MK-801-induced Memory Deficits in Radial Maze Performance in Rats," Brain Research, 1999, vol. 839, pp. 186-189.
Chen Z., et al., "Pharmacological Effects of Carcinine on Histaminergic Neurons in the Brain," British Journal of Pharmacology, 2004, vol. 143, pp. 573-580.
Clapham J., et al., "Thioperamide, the Selective Histamine H3 Receptor Antagonist, Attenuates Stimulant Induced Locomotor Activity in the Mouse," European Journal of Pharmacology, 1994, vol. 259 (2), pp. 107-114.
Cowart M., et al., "4-(2-[2-(2(R)- Methylpyrrolidin-1-yl) ethyl] Benzofuran-5yl) Benzonitrile and Related 2-Aminoethylbenzofuran H3 Receptor Antagonists Potently Enhance Cognition and Attention," Journal of Medicinal Chemistry , 2005, vol. 48 (1), pp. 38-55.
Cowart M., et al., "Pharmacological Characterization of A-960656, a Histamine H3 Receptor Antagonist with Efficacy in Animal Models of Osteoarthritis and Neuropathic Pain," European Journal of Pharmacology, 2012, vol. 684 (1-3), pp. 87-94.
Damasio A.R., "Alzheimer's Disease and Related Dementias" in: Cecil Textbook of Medicine, 20th Edition, Bennett J.C., et al., eds., W.B. Saunders Company, 1996, pp. 1992-1996.
De Almeida M.A., et al., "Memory Facilitation by Histamine," Archives Internationales De Physiologie Et De Biochimie, 1986, vol. 283 (2), pp. 193-198.
Dehmlow E.V., et al., "Stereoselektive Synthese von 3-substituierten Cyclobutanolen und Folgeprodukten," Chemische Berichte, 1993, vol. 126, pp. 2759-2763.
Delaunois A., et al., "Modulation of Acetylcholine, Capsaicin and subsztance P Effects by Histamine $H_3$ Receptors in Isolated Perfused Rabbit Lungs," European Journal of Pharmacology, 1995, vol. 277 (2-3), pp. 243-250.
Dimitriadou V., et al., "Functional Relationship Between Mast Cells and C-Sensitive Nerve Fibres Evidenced by Histamine $H_3$-Receptor Modulation in Rat Lung and Spleen," Clinical Science, 1994, vol. 87, pp. 151-163.
Dumery V., et al., "Development of Amygdaloid Cholinergic Mediation of Passive Avoidance Learning in the Rat," Experimental Brain Research , 1987, vol. 67(1), pp. 61-69.
Dvorak C.A., et al., "4-Phenoxypiperidines: Potent, Conformationally Restricted, non-Imidazole Histamine H3 Antagonists," Journal of Medicinal Chemistry, 2005, vol. 48 (6), pp. 2229-2238.
Esbenshade T.A., et al., "Histamine H3 Receptor Antagonists: Preclinical Promise for Treating Obesity and Cognitive Disorders," Molecular Interventions, 2006, vol. 6 (2), pp. 77-88.
Esbenshade T.A., et al., "Pharmacological and Behavioral Properties of A-349821, a Selective and Potent Human Histamine H3 Receptor Antagonist," Biochemical Pharmacology, 2004, vol. 68 (5), pp. 933-945.

(56) References Cited

OTHER PUBLICATIONS

Esbenshade T.A., et al., "Pharmacological Properties of ABT-239 [4-(2- {2-[(2R)-2-Methylpyrrolidinyl]ethyl}-benzofuran-5-yObenzonitrile]: I. Potent and Selective Histamine H3 Receptor Antagonist with Drug-Like Properties," Journal of Pharmacology and Experimental Therapeutics, 2005, vol. 313 (1), pp. 165-175.
Falmagne J.B., et al., "Cyclobutanone and Cyclobutenone Derivative by Reaction of Tertiary Amides with Alkenes or Alkynes," Angewandte Chemie International Edition, 1981, vol. 20 (10), pp. 879-880.
FDA Mulls Drug to Slow Late-Stage Alzheimer's [online], [retrieved on Sep. 23, 2003]. Retrieved from the Internet:< URL: http://www.cnn.com/2003/HEALTH/conditions/09/24/alzheimers.drug.ap/indexhtml>.
Final Office Action mailed Aug. 8, 2011 for U.S. Appl. No. 11/766,987, filed Jun. 22, 2007.
Fitzsimons C., et al., "Histamine Receptors Signaling in Epidermal Tumor Cell Lines with H-Ras Gene Alterations," Inflammation Research, 1998, vol. 47 (1), pp. S50-S51.
Foley A.G., et al., "H3 Receptor Antagonism Enhances NCAM PSA-Mediated Plasticity and Improves Memory Consolidation in Odor Discrimination and Delayed Match-to-Position Paradigms," Neuropsychopharmacology, 2009, vol. 34 (12), pp. 2585-2600.
Fox G.B., et al., "Effects of Histamine H3 Receptor Ligands GT2331 and Ciproxifan in a Repeated Acquisition Response in the Spontaneously Hypertensive Rat Pup," Behavioural Brain Research, 2002, vol. 131 (1-2), pp. 151-161.
Fox G.B., et al., "Identification of Novel H3 Receptor (H3R) Antagonists with Cognition Enhancing Properties in Rats," Inflammation Research, 2003, vol. 52 (1), pp. S31-S32.
Fox G.B., et al., "Pharmacological Properties of ABT-239 [4-(2-{2-[(2R)-2-Methylpyrrolidinty]ethyl}-benzofuran-5-yl)benzonitrile]-: II Neurophysiological Characterization and Broad Preclinical Efficacy in Cognition and Schizophrenia of a Potent and Selective Histamine H3 R," Journal of Pharmacology and Experimental Therapeutics, 2005, vol. 313 (1), pp. 176-190.
Fox G.B., et al., "Two Novel and Selective Nonimidazole H3 Receptor Antagonists A-304121 and A-317920: II. In Vivo Behavioral and Neurophysiological Characterization," Journal of Pharmacology and Experimental Therapeutics, 2003, vol. 305 (3), pp. 897-908.
Ghosez L., et al., "Intramolecular Cycloadditions of Keteniminium Salts. A Novel Apporach Toward Prostaglandins," Tetrahedron Letters, 1986, vol. 27 (43), pp. 5211-5214.
Glase S.A., et al., "Attention Deficit Hyperactivity Disorder: Pathophysiology and Design of New Treatments," Annual Reports in Medicinal Chemistry, 2002, vol. 37, pp. 11-20.
Haas L., et al., "Subcortical Modulation of Synaptic Plasticity in the Hippocampus," Behavioural Brain Research, 1995, vol. 66 (1-2), pp. 41-44.
Halpern, M.T., "GT-2331," Current Opinion in Central and Peripheral Nervous System Investigational Drugs, vol. 1, pp. 524-527, 1999.
Hancock A.A., et al., "Antiobesity Effects of A-331440, a Novel Non-Imidazole Histamine H3 Receptor Antagonist," European Journal of Pharmacology, 2004, vol. 487 (1-3), pp. 183-197.
Hancock A.A., et al., "Histamine H3 Antagonists in Models of Obesity," Inflammatory Research, 2004, vol. 53 (Suppl. 1), pp. S47-S48.
Harada C., et al., "Inhibitory Effect of Iodophenpropit, a Selective Histamine H3 Antagonist, on Amygdaloid Kindled Seizures," Brain Research Bulletin, 2004, vol. 63 (2), pp. 143-146.
Harada C., et al., "Intracerebroventricular Administration of Histamine H3 Receptor Antagonists Decreases Seizures in Ray Models of Epilepsia," Methods and Findings in Experimental and Clinical Pharmacology, 2004, vol. 26 (4), pp. 263-270.
Higuchi T., et al., eds., Pro-drugs as Novels Delivery Systems, vol. 14, ACS Symposium Series, 1975, Table of Contents.
Houge C., et al., "Models for Asymmetric [2+2] Cycloadditions," Journal of American Chemical Society, 1982, vol. 104, pp. 2920-2921.
Hriscu A., et al., "Experimental Evaluation of the Analgesic Efficacy of Some Antihistamines as Proof of the Histaminergic Receptor Involvement in Pain," Famacia, 2001, vol. 49 (2), pp. 23-30.
Hsieh G.C., et al., "The Histamine H3 Receptor as a Potential Antinociceptive Target: Effects of Selective H3 Antagonists in Several Preclinical Pain Models and the Involvement of Noradrenergic Systems," Global Pharmaceutical Research & Development, 2009, Abbott Laboratories, Abbott Park, IL 60064.
Huang Y.W., et al., "Effect of the Histamine H.sub.3-antagonist Clobenpropit on Spatial Memory Deficits Induced by MK-801 as Evaluated by Radial Maze in Sprague-Dawley Rats," Behavioural Brain Research, 2004, vol. 151 (1-2), pp. 287-293.
International Preliminary Report on Patentability and Written Opinion for Application No. PCT/US2007/071849, mailed on Jan. 6, 2009, 7 pages.
International Preliminary Report on Patentability and Written Opinion for Application No. PCT/US2008/085622, mailed on Jun. 15, 2010, 7 pages.
International Preliminary Report on Patentability and Written Opinion for Application No. PCT/US2010/032488, mailed on Nov. 1, 2011, 6 pages.
International Search Report for Application No. PCT/DK2003/000071, mailed on Jul. 29, 2003, 10 pages.
International Search Report for Application No. PCT/EP2006/063753, mailed on Apr. 27, 2007, 11 pages.
International Search Report for Application No. PCT/EP2008/052430, mailed on May 25, 2009, 5 pages.
International Search Report for Application No. PCT/US2006/021257, mailed on Dec. 15, 2006, 3 pages.
International Search Report for Application No. PCT/US2007/071849, mailed on Jan. 29 2008, 4 pages.
International Search Report for Application No. PCT/US2008/077103, mailed on Apr. 27, 2009, 3 pages.
International Search Report for Application No. PCT/US2008/085622, mailed on Jun. 8, 2009, 6 pages.
International Search Report for Application No. PCT/US2008/085662, mailed on Jun. 8, 2009, 4 pages.
International Search Report for Application No. PCT/US2009/033062, mailed on Sep. 1, 2009, 4 pages.
International Search Report for Application No. PCT/US2009/033329, mailed on Sep. 17, 2009, 3 pages.
International Search Report for Application No. PCT/US2011/051603, mailed on Dec. 5, 2011, 5 pages.
Itoh E., et al., "Thioperamide, A Histamine H.sub.3 Receptor Antagonist, Powerfully Suppresses Peptide YY-Induced Food Intake in Rats," Biological Psychiatry, 1999, vol. 45 (4), pp. 475-481.
Jantzen, et al., Modern Pharmacueticals, 1996, pp. 596.
Kallemeyn J.M., et al., "Asymmetric Synthesis of Di- and Trisubstituted Cyclopropanes Through an Intramolecular Ring Closure," Synlett, 2011, vol. 4, pp. 535-538.
Kallemeyn J.M., et al., ChemInform, 2011, vol. 42 (26), 4 pages.
Kamei C., et al., "Influence of Certain H.sub.1-Blockers on the Step-Through Active Avoidance Response in Rats," Psychopharmacology, 1990, vol. 102 (3), pp. 312-318.
Kamei C., et al., "Participation of Histamine in the Step-Through Active Avoidance Response and Its Inhibition by H.sub.1-Blockers," Japan Journal of Pharmacology, 1991, vol. 57 (4), pp. 473-482.
Kauffmann T., et al., "Home Aldehydselektivitat Bei Carbonylolefinierungen MIT Titan- Und Chrom-Reagenzien," Tetrahedron Letters, 1981, vol. 22 (50), pp. 5031-5034.
Komater V.A., et al., "H3 Receptor Blockade by Thioperamide Enhances Cognition in Rats without Inducing Locomotor Sensitization," Psychopharmacology, 2003, vol. 167 (4), pp. 363-372.
Krepski L.R., et al., "An Improved Procedure for the Addition of Dichloroketene to Unreactive Olefins," Journal of Organic Chemistry, 1978, vol. 43 (14), pp. 2879-2882.
Krueger K.M., et al., "G Protein-Dependent Pharmacology of Histamine H3 Receptor Ligands: Evidence for Heterogeneous Active State Receptor Conformations," Journal of Pharmacology and Experimental Therapeutics, 2005, vol. 314 (1), pp. 271-281.

(56) References Cited

OTHER PUBLICATIONS

Lamberti C., et al., "Antidepressant-like Effects of Endogenous Histamine and of Two Histamine H 1 Receptor Agonists in the Mouse Forced Swim Test," British Journal of Pharmacology, 1998, vol. 123 (7), pp. 1331-1336.
Layzer R.B., "Degenerative Diseases of the Nervous System" in: Cecil Textbook of Medicine, 20th Edition, Bennett J.C., et al., eds., W.B. Saunders Company, 1996, pp. 2050-2057.
Leurs R., et al., eds., "The Histamine H3 Receptor: A Target for New Drugs," vol. 30, Elsevier Science B.V., 1998, Table of Contents.
Leurs R., et al., "En Route to New Blockbuster Anti-Histamines: Surveying the Offspring of the Expanding Histamine Receptor Family," Trends in Pharmacological Sciences, 2011, vol. 32 (4), pp. 250-257.
Leurs R., et al., "Histamine Homologues Discriminating between Two Functional $H_3$-Receptor Assays. Evidence for $H_3$ Receptor," Journal of Pharmacology and Experimental Therapeutics, 1996, vol. 276 (3), pp. 1009-1015.
Leurs R., et al., The Histamine H3-Receptor: A Target for Developing New Drugs, Elsevier Science, 1998, vol. 39, pp. 127-165.
Leurs R., et al., "The Medicinal Chemistry and Therapeutic Potentials of Ligands of the Histamine $H_3$ Receptor," Progress in Drug Research, 1995, vol. 45, pp. 107-165.
Li S.W., et al., "A Novel Methylenation Method of Aldehydes Mediated by Dibutyl Telluride," Chemische Berichte, 1990, vol. 123, pp. 1441-1442.
Ligneau X., et al., "Neurochemical and Behavioral Effects of Ciproxifan, a Potent Histamine H3-Receptor Antagonist," Journal of Pharmacology and Experimental Therapeutics, 1998, vol. 287 (2), pp. 658-666.
Lin J.S., et al., "Involvement of Histaminergic Neurons in Arousal Mechanisms Demonstrated with $H_3$-Receptor Ligands in the Cat," Brain Research, 1990, vol. 523 (2), pp. 325-330.
Lozada A.F., et al., "Plasticity of Histamine $H_3$ Receptor Expression and Binding in the Vestibular Nuclei After Labyrinthectomy in Rat," Biomedical Center Neuroscience, 2004, vol. 5, pp. 32.
Malmberg Aiello P., et al., "Role of Histamine in Rodent Antinociception," British Journal of Pharmacology, 1994, vol. 111 (4), pp. 1269-1279.
Marko I., et al., "Intramolecular [2+2] Cycloadditions of Ketenes and Keteniminium Salts to Olefins," Journal of the American Chemical Society, 1985, vol. 107, pp. 2192-2194.
Mazurkiewicz-Kwilecki I.M., et al., "Changes in the Regional Brain Histamine and Histidine Levels in Postmortem Brains of Alzheimer Patients," Canadian Journal of Physiology and Pharmacology, 1989, vol. 67 (1), pp. 75-78.
McLeod R.L., et al., "Combined Histamine H1 and H3 Receptor Blockade Produces Nasal Decongestion in an Experimental Model of Nasal Congestion," American Journal of Rhinology, 1999, vol. 13 (5), pp. 391-399.
McLeod R.L., et al., "Histamine $H_3$ Antagonists," Progress in Respiratory Research, 2001, vol. 31, pp. 133-136.
Medhurst A.D., et al., "GSK189254, a Novel H3 Receptor Antagonist that Binds to Histamine H3 Receptors in Alzheimer's Disease Brain and Improves Cognitive Performance in Preclinical Models," Journal of Pharmacology and Experimental Therapeutics, 2007, vol. 321 (3), pp. 1032-1045.
Meguro K., et al., "Effects of Thioperamide, a Histamine H3 Antagonist, on the Step-Through Passive Avoidance Response and Histidine Decarboxylase Activity in Senescence-Accelerated Mice," Pharmacology, Biochemistry and Behavior, 1995, vol. 50 (3), pp. 321-325.
Monti J., et al., "Sleep and Waking During Acute Histamine $H_3$ Agonist BP2.94 or $H_3$ Antagonist Carboperamide (MR 16155) Administration in Rats," Neuropsychopharmacology, 1996, vol. 15 (1), pp. 31-35.
Monti J.M., et al., "Effects of Selective Activation or Blockade of the Histamine $H_3$ Receptor on Sleep and Wakefulness," Journal of Pharmacology, 1991, vol. 205, pp. 283-287.

Morisset S., et al., "Atypical Neuroleptics Enhance Histamine Turnoer in Brain Via 5-Hydroxytryptamino$_{2A}$ Receptor Blockade," Journal of Pharmacology and Experimental Therapeutics, 1999, vol. 288 (2), pp. 590-596.
Mulhern, et al., "Asymmetric Synthesis of Di- and Trisubstituted Cyclopropanes Through an Intramoleculiar Ring Closure," Poster and Abstract, Aug. 24, 2010.
Murakami K., et al., "AQ-0145, A Newly Developed Histamine $H_3$ Antagonist, Decreased Seizure Susceptibility of Electrically Induced Convulsions in Mice," Methods and Findings in Experimental and Clinical Pharmacology, 1995, vol. 17 Suppl C, pp. 70-73.
Njar, "High-Yields Synthesis of Novel Imidazoles and Triazoles form Alcohols and Phenols," Synthesis, 2000, pp. 2019-2028.
Office Action mailed Jan. 7, 2011 for U.S. Appl. No. 11/766,987, filed Jun. 22, 2007.
Office Action mailed Oct. 7, 2010 for U.S. Appl. No. 11/956,816, filed Dec. 14, 2007.
Office Action mailed Sep. 8, 2008 for U.S. Appl. No. 11/766,987, filed Jun. 22, 2007.
Office Action mailed Jan. 9, 2009 for U.S. Appl. No. 11/766,987, filed Jun. 22, 2007.
Office Action mailed Oct. 19, 2009 for U.S. Appl. No. 11/766,987, filed Jun. 22, 2007.
Office Action mailed Mar. 22, 2010 for U.S. Appl. No. 11/956,816, filed Dec. 14, 2007.
O'Neill A.B., et al., "Pharmacological Evaluation of the In Vivo Model of Vestibular Dysfunction in the Rat," Methods and Findings in Experimental and Clinical Pharmacology, 1999, vol. 21 (4), pp. 285-289.
Onodera K., et al., "Improvement by FUB 181, A Novel Histamine H 3 -Receptor Antagonist, of Learning and Memory in the Elevated Plus-Maze Test in Mice," Naunyn-Schmiedebergs' Archives of Pharmacology, 1998, vol. 357 (5), pp. 508-513.
Onodera K., et al., "Neuropharmacology of the Histaminergic Neuron System in the Brain and its Relationship with Behavioral Disorders," Progress in Neurobiology, 1994, vol. 42 (6), pp. 685-702.
Pan J.B., et al., "Histaminergic Ligands Attenuate Barrel Rotation in Rats Following Unilateral Labyrinthectomy," Methods and Findings in Experimental and Clinical Pharmacology, 1998, vol. 20 (9), pp. 771-777.
Panula P., et al., "Neuronal Histamine Deficit in Alzheimer's Disease," Neuroscience, 1998, vol. 82 (4), pp. 993-997.
Passani M.B., et al., "Central Histaminergic System and Cognition," Neuroscience and Biobehavioral Reviews, 2000, vol. 24 (1), pp. 107-113.
Pelter A., et al., "Reductive Aminations of Ketones and Aldehydes using Borane-Pyridine," Journal of the Chemical Society, 1984, vol. 4, pp. 717-720.
Penning T.D., et al., "Structure-Activity Relationship Studies on 142-(4-Phenylphenoxy)ethly]pyrrolidine (SC-22716), a Potent Inhibitor of Leukotriene $A_4$ ($LTA_4$) Hydrolase," Journal of Medicinal Chemistry, 2000, vol. 43 (4), pp. 721-735.
Perez-Garcia C., et al., "Effects of Histamine $H_3$ Receptor Ligands in Experimental Models of Anxiety and Depression," Psychopharmacology, 1999, vol. 142 (2), pp. 215-220.
Prast H., et al., "Histaminergic Neurons Facilitate Social Memory in Rats," Brain Research, 1996, vol. 734 (1-2), pp. 316-318.
Prodrug [online], [retrieved on Mar. 26, 2007]. Retrieved from the Internet< URL: http://en.wikipedia.org/wiki/Prodrug>.
Pu Y.M., et al., "A Facile and Scaleable Synthesis of ABT-239, A Benzofuranoid H3 Antagonist," Organic Process Research and Development, 2005, vol. 9, pp. 45-50.
Roche E.B., ed., Bioreversible Carries in Drug Design Theory and Application, Pergamon Press, 1987, Table of Contents.
Rodrigues A.A., et al., "Interaction of Clozapine with the Histamine H3 Receptor in Rat Brain," British Journal of Pharmacology, 1995, vol. 114 (8), pp. 1523-1524.
Sakai N., et al., "Effects of Thioperamide, A Histamine H3 Receptor Antagonist, on Locomotor Activity and Brain Histamine Content in Mast Cell-Deficient Wiwv Mice," Life Sciences, 1991, vol. 48 (25), pp. 2397-2404.

(56) References Cited

OTHER PUBLICATIONS

Sakata T., et al., "Hypothalamic Neuronal Histamine Modulates Ad Libitum Feeding by Rats," Brain research, 1990, vol. 537 (1-2), pp. 303-306.

Sanchez-Lemus E., et al., "Histamine H.Sub.3 Receptor Activation Inhibits Dopamine D.Sub.1 Receptor-Induced Camp Accumulation in Rat Striatal Slices," Neuroscience Letters, 2004, vol. 364 (3), pp. 179-184.

Schwartz J., et al., "Histamine", in: Psychopharmacology: The Fourth Generation of Progress, Chapter 35, Bloom F.E., et al., eds., Raven Press, 1995, pp. 397-405.

Schweitzer J.B., et al., "Drugs Under Investigation for Attention-Deficit Hyperactivity Disorder," Current Opinion in Investigational Drugs, 2002, vol. 3 (8), pp. 1207-1211.

Shah C., et al., "Novel Human Histamine H3 Receptor Antagonists," Bioorganic & Medicinal Chemistry Letters, 2002, vol. 12 (22), pp. 3309-3312.

Shaywitz B.A., et al., "Dopaminergic But Not Noradrenergic Mediation of Hyperactivity and Performance Deficits in the Developing Rat Pup," Psychopharmacology, 1984, vol. 82 (1-2), pp. 73-77.

Srivastava R.R., et al., "4-Dihydroxyborylphenyl Analogues of 1-Aminocyclobutanecarboxylic Acids: Potential Boron Neutron Capture Therapy Agents," Journal of Organic Chemistry, 1999, vol. 64, pp. 8495-8500.

Szelag A., "Role of Histamine H.Sub.3-Receptors in the Proliferation Neoplastic Cells in Vitro," Medical Science Monitor, 1998, vol. 4 (5), pp. 747-755.

Tedford C.E., "Pharmacological Characterization of Gt-2016, A Non-Thiourea-Containing Histamine H.Sub.3 Antagonist: in Vitro and in Vivo Studies," The Journal of Pharmacology and Experimental Therapeutics, 1995, vol. 275 (2), pp. 598-604.

Tedford et al., "Cognition and Locomotor Activity in the Developing Rat: Comparisons of Histamine H.sub.3 Receptor Antagonists and ADHD Therapeutics," Society for Neuroscience Abstr, vol. 22, pp. 22, 1996.

Tozer M., et al., "Histamine H3 Receptor Antagonists," Expert Opinion Therapeutic Patents, 2000, vol. 10 (7), pp. 1045-1055.

Vohora D., et al., "Thioperamide, A Selective Histamine H.sub.3 Receptor Antagonist, Protects Against PTZ-Induced Seizures in Mice," Life Sciences, 2000, vol. 66 (22), pp. PL297-PL301.

Wada H., et al., "Is the Histaminergic Neuron System a Regulatory Center for Whole-Brain Activity", Trends in Neurosciences, 1991, vol. 14 (9), pp. 415-418.

Wang Y., et al., "Design and Synthesis of Ether Analogues as Potent and Selective M2 Muscarinic Receptor Antagonists," Bioorganic and Mechanical Chemistry Letters, 2001, vol. 11 (7), pp. 891-894.

Yates, S.L., et al., "Effects of a novel histamine H3 receptor antagonist, GT2394, on food intake and weight gain in Sprague-Dawley rats,"Society for Neuroscience, vol. 102 (10), pp. 219, 2000.

Yates S.L., et al., "Identification and Pharmacological Characterization of a Series of New 1H- 4-Substituted-Imidazoyl Histamine H3 Receptor Ligands," Journal of Pharmacology and Experimental Therapeutics, 1999, vol. 289 (2), pp. 1151-1159.

Yawata I., et al., "Role of Histaminergic Neurons in Development of Epileptic Seizures in El Mice," Brain Research. Molecular Brain Research, 2004, vol. 132 (1), pp. 13-17.

Yokoyama H., et al., "Clobenpropit (Vuf-9153), a New Histamine H3 Receptor Antagonist, Inhibits Electrically Induced Convulsions in Mice," European Journal of Pharmacology, 1994, vol. 260 (1), pp. 23-28.

Yokoyama H., et al., "Effect of Thioperamide, a Histamine H3 Receptor Antagonist, on Electrically Induced Convulsions in Mice," Journal of Pharmacology, 1993, vol. 234 (1), pp. 129-133.

Yokoyama H., et al., "Histamine and Seizures Implications for the Treatment of Epilepsy,"CNS Drugs, 1996, vol. 5 (5), pp. 321-330.

Zhang X., et al., "Trans-1-[(2-Phenylcyclopropyhmethyl]-4-arylpiperazines: Mixed Dopamine D(2)/D(4) Receptor Antagonists as Potential Antipsychotic Agents," Journal of Medicinal Chemistry, 2000, vol. 43 (21), pp. 3923-3932.

Kozma et al., "Complexity of Pain Management Among Patients with Nociceptive or Neuropathic Neck, Back, or Osteoarthritis Diagnoses," J. Manag. Care Pharm., 20(5): 455-466 (2014).

\* cited by examiner

TREATMENT OF OSTEOARTHRITIS PAIN

CROSS-REFERENCES TO RELATED APPLICATIONS

This application claims priority to U.S. patent application Ser. No. 61/173,132, filed Apr. 27, 2009, and U.S. patent application Ser. No. 61/173,161, filed Apr. 27, 2009, which are hereby incorporated by reference.

STATEMENT REGARDING FEDERALLY SPONSORED RESEARCH OR DEVELOPMENT

Not applicable.

BACKGROUND OF THE INVENTION

1. Technical Field of the Invention

The invention relates a method of treatment of osteoarthritis pain. The method more particularly relates to the treatment of osteoarthritis pain by administration of a histamine $H_3$ receptor antagonist, a salt thereof, or a composition comprising such compound or salt.

2. Description of Related Technology

Pain of various different types afflicts virtually all humans and animals at one time or another. A substantial number of medical disorders and conditions produce some sort of pain as a prominent concern requiring treatment. Pain is the one of the most common significant medical issues reported in the clinic and it affects the broadest group of patients. Distinct types and manifestations of pain are reported. Different pain types can be related to the origin of the pain, the underlying pathology, or different pharmacological agents that demonstrate efficacy (or lack thereof) in treating the pain.

The pain can be caused by different reasons. For example, the prominent causes of inflammatory pain are burns and chemical irritation. Post-surgical pain can arise after incisions of the skin and internal organs, among other conditions. Nerve damage can lead to neuropathic pain and neuropathy arising from sciatic nerve irritation, chronic diabetes, and chemotherapy. Osteoarthritis pain typically arises from a cause having physical origin, for example, such as the erosion of joint cartilage with a resulting mechanical irritation of the bones and joint.

Various types of pain are treated with distinct, different therapeutic agents. For example, acute inflammatory pain is typically treated with non-steroidal anti-inflammatory (NSAID) agents and cyclooxygenase inhibitors, for example aspirin or celecoxib. Post-surgical pain is typically treated with opiate receptor agonists, for example codeine. Neuropathic pain can be treated with anti-depressant agents and neurotransmitter reuptake inhibitors, for example duloxetine. Osteoarthritis pain is commonly treated with acetaminophen.

A distinct type of pain where patients are not completely treatable by any of the currently available drugs or by agents is neuropathic pain. The drug duloxetine can usefully provide partial relief of this type of pain. Neuropathic pain can develop in response to previous injury or ongoing tissue injury, nerve injury, or diabetes. Neuropathic pain is distinct from other types of pain, for example inflammatory pain, in that it persists long after signs of the original injury or damage have disappeared. Neuropathic pain also is associated with allodynia, hyperalgesia, or causalgia (Dworkin Clinical Journal of Pain (2002) vol. 18(6) pp. 343-9). The topic and physiology of neuropathic pain has been reviewed in the scientific literature (Smith, et al. Drug Development Research (2001) vol. 54(3), pp. 140-153; Collins and Chessell Expert Opinion on Emerging Drugs (2005) vol. 10(1), pp. 95-108; Vinik and Mehrabyan Medical Clinics of North America (2004), vol. 88(4), pp. 947-999; Dray, Urban, and Dickenson Trends in Pharmacological Sciences (1994) vol. 15(6) pp. 190-7; Dworkin Clinical Journal of Pain (2002) vol. 18(6) pp. 343-9.) Some histamine $H_3$ receptor antagonists have been reported to have efficacy in animal models of neuropathic pain (Medhurst, et al. Biochemical Pharmacology (2007) 73, pp. 1182-1194; Medhurst, et al. Pain (2008) 138, pp. 61-69).

A very wide variety of compounds with $H_3$ receptor antagonist activity has been reported (Berlin and Boyce, Expert Opinion in Therapeutic Patents (2007) 17(6) pp. 675-687; Esbenshade, Browman, Bitner, Strakhova, Cowart, and Brioni, Br. J. Pharmacol. (2008), 154, pp. 1166-1181.) Different $H_3$ antagonists have been found active in models of specific human diseases, including for example, Alzheimer's disease, age-related cognitive and memory impairment, attention-deficit hyperactivity disorder, cognitive disfunction related to schizophrenia, allergic rhinitis, and sleep disorders.

In contrast to neuropathic pain, pain from osteoarthritis is thought to arise first from some structural pathology, and then from damage or destruction of the cartilage and alteration of the joint surface. Consequent mechanical irritation of nerves in bones and joints leads to pathological sensitization of peripheral and central nerves (Dray and Read, Arthritis Research and Therapy (2007) 9, p. 212). The pain of osteoarthritis in the clinic is independent of ongoing inflammation (Fernihough, et al. Pain (2004) 112, pp. 83-93; Joshi and Honore, Expert Opinion in Drug Discovery (2006), 1(4), pp. 323-334). As yet, there is no pharmacological therapy that reverses the damage to the joint in osteoarthritis. As such, therapeutic agents of diverse pharmacological mechanisms are used to treat the pain symptoms of osteoarthritis. These agents are associated with either incomplete relief of pain or mechanism- and agent-based side effects that compromise the quality of the treatment (Rubin, Journal of the American Osteopathic Association (2005) 105, S23-S28; Dray and Read, Arthritis Research and Therapy (2007) 9, p. 212). As such, it would be particularly beneficial to identify new methods for treating osteoarthritis. It would be particularly beneficial if such methods are based on previously unexplored mechanisms for pain treatment that may offer improved pain relief or are less associated with side effects. However, no $H_3$ antagonist has yet been reported to demonstrate effect in osteoarthritis pain.

SUMMARY OF THE INVENTION

The invention relates a method of treatment of osteoarthritis pain. The method more particularly relates to the treatment of osteoarthritis pain by administration of a histamine $H_3$ receptor antagonist, a salt thereof, or a composition comprising such sompound or salt.

Suitable histamine $H_3$ antagonists are, for example, compounds of formula:

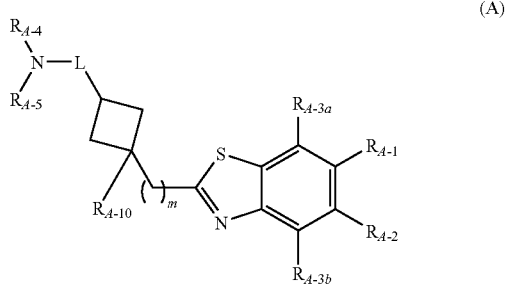

or a pharmaceutically acceptable salt thereof, wherein:
m is 0 or 1;
one of $R_{A-1}$ and $R_{A-2}$ is hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, haloalkoxy, haloalkyl, halogen, hydroxy, hydroxyalkyl, mercapto, nitro, alkylthio, —$NR_{A-A}R_{A-B}$, $(NR_{A-A}R_{A-B})$carbonyl, —$SO_2N(R_{A-14a})(R_{A-14b})$, $N(R_{A-14a})SO_2(R_{A-14b})$, a group of the formula -$L_{A-2}$-$R_{A-6}$, or a group of the formula -$L_{A-3a}$-$R_{A-6a}$-$L_{A-3b}$-$R_{A-6b}$;

the other of $R_1$ and $R_2$ is selected from hydrogen, cyano, halogen, alkyl, cycloalkyl, fluoroalkyl, alkoxy, alkoxyalkyl, fluoroalkoxy, alkylthio, —$SO_2N(R_{A-14a})(R_{A-14b})$, and —$N(R_{A-14a})SO_2(RA_{A-14b})$;

$R_{A-3a}$ and $R_{A-3b}$ are each independently selected from hydrogen, cyano, halogen, alkyl, cycloalkyl, fluoroalkyl, alkoxy, alkoxyalkyl, fluoroalkoxy, alkylthio, —$SO_2N(R_{A-14a})(R_{A-14b})$, and —$N(R_{A-14a})SO_2(R_{A-14b})$;

$R_{A-4}$ and $R_{A-5}$ are each independently selected from alkyl, fluoroalkyl, hydroxyalkyl, alkoxyalkyl, and cycloalkyl; or $R_{A-4}$ and $R_{A-5}$ taken together with the nitrogen atom to which each is attached form a non-aromatic ring;

$R_{A-6}$ is selected from aryl, heterocycle, and heterocyclealkyl;

$R_{A-6a}$ is selected from aryl and heterocycle;

$R_{A-6b}$ is selected from aryl and heterocycle;

L is a bond or alkylene;

$L_2$ is selected from a bond, —O—, alkylene, —C(=O)—, —S—, —$SO_2N(R_{A-14a})$—, —$N(R_{A-14a})SO_2$—, —C(O)N$(R_{A-14a})$—, —$N(R_{A-14a})C(O)$—, and —$N(R_{A-15})$—;

$L_{3a}$ and $L_{3b}$ are each independently selected from a bond, —O—, alkylene, —C(=O)—, —S—, —$SO_2N(R_{A-14a})$—, —$N(R_{A-14a})SO_2$—, —C(O)N$(R_{A-14a})$—, —$N(R_{A-14a})C(O)$—, and —$N(R_{A-15})$—;

$R_{A-10}$ is selected from hydrogen, cyano, fluoro, hydroxy, and alkyl;

$R_{A-14a}$ and $R_{A-14b}$ are each independently selected at each occurrence from hydrogen, alkyl, and cycloalkyl;

$R_{A-15}$ is selected from hydrogen, alkyl, acyl, alkoxycarbonyl and $(R_{A-14a})(R_{A-14b})NC(O)$—; and $R_{A-A}$ and $R_{A-B}$ are independently selected from hydrogen, alkyl, acyl, haloalkyl, alkoxycarbonyl, cycloalkyl, and formyl.

Such compounds, salts, and methods for preparing them are described in US Patent Publication No. 2007/0066588, published Mar. 22, 2007, and the related U.S. Pat. No. 7,576,110, issued Aug. 18, 2009, both the contents of which are herein incorporated by reference. Compounds generally and specifically useful in the invention are described in US Patent Publication No. 2007/0066588, published Mar. 22, 2007. Some specific compounds of interest, are for example, (S)-3-hydroxy-1-[2-(3-piperidin-1-yl-cyclobutyl)-benzothiazol-6-yl]-pyrrolidin-2-one, trans-2-[2-(3-piperidin-1-ylcyclobutyl)-1,3-benzothiazol-6-yl]pyridazin-3(2H)-one, and cis-2-[2-(3-piperidin-1-ylcyclobutyl)-1,3-benzothiazol-6-yl]pyridazin-3(2H)-one.

Other suitable histamine $H_3$ antagonists are, for example, compounds of formula:

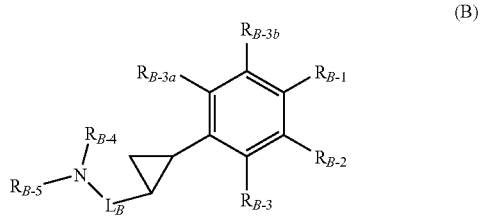

(B)

or a pharmaceutically acceptable salt thereof, wherein one of $R_{B-1}$ and $R_{B-2}$ is a group of the formula -$L_{B-2}$-$R_{B-6a}$-$L_{B-3}$-$R_{B-6b}$;

the other of $R_{B-1}$ and $R_{B-2}$ is selected from hydrogen, alkyl, alkoxy, halogen, cyano, and thioalkoxy;

$R_{B-3}$, $R_{B-3a}$, and $R_{B-3b}$ are each independently selected from the group consisting of hydrogen, alkyl, trifluoroalkyl, trifluoroalkoxy, alkoxy, halogen, cyano, and thioalkoxy $R_{B-4}$ and $R_{B-5}$ are each independently selected from alkyl, fluoroalkyl, hydroxyalkyl, alkoxyalkyl, and cycloalkyl, or $R_{B-4}$ and $R_{B-5}$ taken together with the nitrogen atom to which each is attached form a non-aromatic ring of the formula:

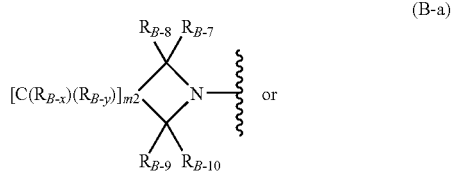

(B-a)

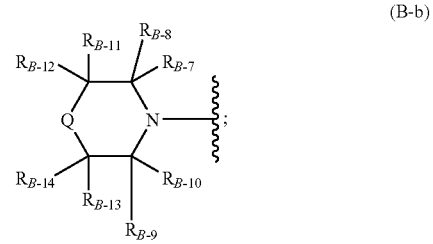

(B-b)

$R_{B-7}$, $R_{B-8}$, $R_{B-9}$, and $R_{B-10}$ at each occurrence are each independently selected from hydrogen, hydroxyalkyl, fluoroalkyl, cycloalkyl, and alkyl;

$R_{B-11}$, $R_{B-12}$, $R_{B-13}$, and $R_{B-14}$ are each independently selected from hydrogen, hydroxyalkyl, alkyl, and fluoroalkyl;

$R_{B-6a}$ is selected from a 5- to 6-membered heteroaryl ring, cyanophenyl, an 8- to 12-membered bicyclic heteroaryl ring, and a 4- to 12-membered heterocyclic ring;

$R_{B-6b}$ is selected from hydrogen, a 5- to 6-membered heteroaryl ring, an aryl ring, an 8- to 12-membered bicyclic heteroaryl ring, and a 4- to 12-membered heterocyclic ring;

Q is selected from O and S;

$L_B$ is —$[C(R_{B-16})(R_{B-17})]_k$;

$L_2$ is selected from a bond, alkylene, —O—, —C(=O)—, —S—, —NH—, —$N(R_{B-16})C(=O)$—, —$C(=O)N(R_{B-16})$, and —N(alkyl)-;

$L_3$ is selected from a bond, alkylene, —O—, —C(=O)—, —S—, —$N(R_{B-16})C(=O)$—, —$C(=O)N(R_{B-16})$, and —$N(R_{B-15})$—;

$R_{B-15}$ is selected from hydrogen, alkyl, acyl, alkoxycarbonyl, amido, and formyl;

$R_{B-16}$ and $R_{B-17}$ at each occurrence are independently selected from hydrogen and alkyl;

$R_{B-x}$ and $R_{B-y}$ at each occurrence are independently selected from hydrogen, hydroxy, alkyl, alkoxy, alkylamino, fluoro, and dialkylamino;

k is 1, 2, or 3; and m2 is an integer from 1 to 5.

Such compounds, salts, and methods for preparing them are described in US Patent Publication No. 2008/0242653, published Oct. 2, 2008, the contents of which are herein incorporated by reference. Compounds generally and specifically, as well as the salts thereof, useful in the invention are described in US Patent Publication No. 2008/0242653, published Oct. 2, 2008. A preferred compound of interest is 2-[4-((1S,2S)-2-{[(2S)-2-methylpyrrolidin-1-yl]methyl}cyclopropyl)phenyl]pyridazin-3(2H)-one.

Other suitable histamine H$_3$ antagonists are, for example, compounds of formula:

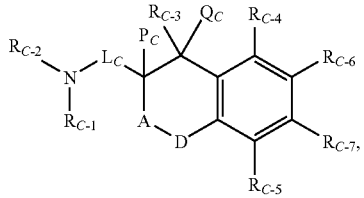

(C)

or a pharmaceutically acceptable salt, wherein

A is selected from the group consisting of carbonyl and a covalent bond;

D is selected from the group consisting of O and S;

L is selected from the group consisting of lower alkylene, fluoroalkylene, and hydroxyalkylene;

$P_C$ and $Q_c$ taken together form a covalent bond or are both hydrogen;

$R_{C-1}$ and $R_{C-2}$ are each independently selected from the group consisting of hydrogen, alkyl, aryl, arylalkyl, cycloalkyl, cycloalkylalkyl, heterocycle, heterocyclealkyl, hydroxyalkyl, alkenyl, and alkynyl; or $R_{C-1}$ and $R_{C-2}$ taken together with the nitrogen atom to which they are attached, together form a heterocycle;

$R_{C-3}$ is selected from the group consisting of hydrogen, alkoxy, alkoxycarbonyl, alkyl, alkylcarbonyl, alkylcarbonyloxy, alkylsulfinyl, alkylsulfonyl, alkylthio, aryl, carboxy, carboxyalkyl, cyano, cyanoalkyl, formyl, halogen, haloalkoxy, haloalkyl, heterocycle, hydroxy, hydroxyalkyl, mercapto, nitro, —NR$_{C-A}$R$_{C-B}$, (NR$_{C-A}$R$_{C-B}$)alkyl, (NR$_{C-A}$R$_{C-B}$)carbonyl, and (NR$_{C-A}$R$_{C-B}$)sulfonyl;

$R_{C-4}$, $R_{C-5}$, $R_{C-6}$ and $R_{C-7}$ are each independently selected from the group consisting of hydrogen, alkoxy, alkoxycarbonyl, alkyl, alkylcarbonyl, alkylcarbonyloxy, alkylsulfinyl, alkylsulfonyl, alkylthio, aryl, carboxy, carboxyalkyl, cyano, cyanoalkyl, cycloalkyl, formyl, halogen, haloalkoxy, haloalkyl, heterocycle, hydroxy, hydroxyalkyl, mercapto, nitro, —NR$_{C-A}$R$_{C-B}$, (NR$_{C-A}$R$_{C-B}$)alkyl, (NR$_{C-A}$R$_{C-B}$)carbonyl, (NR$_{C-A}$R$_{C-B}$)sulfonyl, -L$_{C-2}$R$_{C-20}$, and —R$_{C-21}$L$_{C-3}$R$_{C-22}$;

$L_{C-2}$ is selected from the group consisting of alkylene, alkenylene, O, S, S(O), S(O)$_2$, C(=O), C=(NOR$_{C-21}$), and N(R$_{C-A}$);

$L_3$ is selected from the group consisting of a covalent bond, alkylene, alkenylene, O, S, C(=O), N(=OR$_{C-21}$), and N(R$_{C-A}$);

$R_{C-20}$ is selected from the group consisting of aryl, heterocycle, and cycloalkyl;

$R_{C-21}$ is selected from the group consisting of hydrogen and alkyl;

$R_{C-22}$ is selected from the group consisting of aryl, heterocycle, and cycloalkyl;

$R_{C-A}$ and $R_{C-B}$ are each independently selected from the group consisting of hydrogen, alkyl, alkylcarbonyl and formyl;

provided that at least one of $R_{C-4}$, $R_{C-5}$, $R_{C-6}$, or $R_{C-7}$ is aryl, heterocycle, cycloalkyl, -L$_{C-2}$R$_{C-20}$ or —R$_{C-20}$L$_{C-3}$R$_{C-22}$.

Such compounds, salts, and method for preparing them are described in U.S. Pat. No. 6,969,730, issued Nov. 29, 2005, the contents of which are herein incorporated by reference. Compounds generally and specifically, as well as the salts thereof, useful in the invention are described in U.S. Pat. No. 6,969,730, issued Nov. 29, 2005. A specific compound of interest, is (4-(2-(2-[2(R)-methyl-1-pyrrolidinyl]ethyl)-1-benzofuran-5-yl)benzonitrile) (ABT-239).

Other suitable histamine H$_3$ antagonists are, for example, compounds of formula:

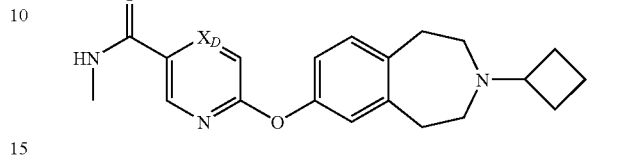

(D)

wherein $X_D$ is CH or N, or a pharmaceutically acceptable salt thereof. Such compounds, salts, and methods for preparing them are described in WO2004/056369, published Jul. 8, 2004, the contents of which are herein incorporated by reference. Compounds generally and specifically, as well as the salts thereof, useful in the invention are described in US20070299056, published Dec. 27, 2007, the contents of which are herein incorporated by reference. Specific compounds of interest are, for example, 6-(3-cyclobutyl-2,3,4,5-tetrahydro-1H-benzo[d]azepin-7-yloxy)-N-methyl-nicotinamide or GSK-189254 and 5-(3-cyclobutyl-2,3,4,5-tetrahydro-1H-benzo[d]azepin-7-yloxy)-N-methylpyrazine-2-carboxamide or GSK-207040.

Other suitable histamine H$_3$ antagonists are, for example, compounds of structure:

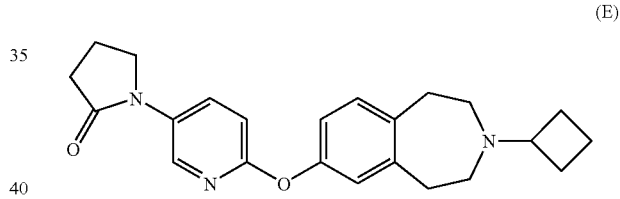

(E)

or 1-{6-[(3-cyclobutyl-2,3,4,5-tetrahydro-1H-3-benzazepin-7-yl)oxy]-3-pyridinyl}-2-pyrrolidinone, and pharmaceutically acceptable salts thereof. Such compound, salts, and method of preparing them are described in WO2008/104590, published Sep. 4, 2008, WO2004/056369, published Jul. 8, 2004, and US 20070299056, published Dec. 27, 2007, the contents of which are all herein incorporated by reference.

Other suitable histamine H$_3$ antagonists are, for example, compounds of structure:

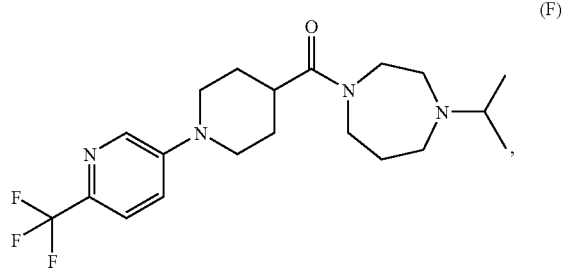 [SMILES: CC(C)N1CCCN(C(=O)C2CCN(c3ccc(C(F)(F)F)nc3)CC2)CC1 ; ","]

(F)

(4-isopropyl-1,4-diazepan-1-yl)(1-(6-(trifluoromethyl)pyridin-3-yl)piperidin-4-yl)methanone, or GSK-334429, and pharmaceutically acceptable salts thereof. Such compounds, salts, and method of preparing them are described in WO2004/101546, published Nov. 25, 2004, the contents of which are herein incorporated by reference.

Other suitable histamine $H_3$ antagonists are, for example, compounds of formula:

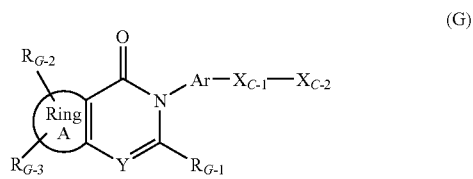

(G)

wherein Ar is a divalent group formed by eliminating two hydrogen atoms from benzene, pyrimidine, pyridine, thiazole, oxazole, pyrazole, thiadiazole or thiophene (this divalent group may be further substituted by a halogen atom, lower alkoxy (this lower alkoxy group may be further substituted by halogen), hydroxy or lower alkyl); $X_1$ is a nitrogen atom, sulfur atom or oxygen atom; $R_{G-1}$ is a 5- or 6-membered heteroaryl group having 1 to 4 heteroatoms selected from among nitrogen, sulfur and oxygen, heteroarylalkyl group (heteroaryl in this group has the same meaning as the above), straight chain or branched lower alkyl (this lower alkyl group may be further substituted by hydroxy, halogen, alkoxy, allyloxy or aralkyloxy), phenyl, aralkyl, alkoxy, alkylthio or lower alkylamino; Ring A is a 5- or 6-membered heteroaryl ring having 1 or 2 nitrogen atoms or sulfur atoms in the ring, or a benzene ring; $R_2$ and $R_3$ may be the same or different, and each represents hydrogen, amino, alkylamino, dialkylamino, nitro, cyano, hydroxy, lower alkylsulfonyl, halogen, lower alkyl (this lower alkyl group may be further substituted by halogen), lower cycloalkyl (this lower cycloalkyl group may be further substituted by halogen), lower alkoxy (this lower alkoxy group may be further substituted by halogen or hydroxy), lower cycloalkoxy (this lower cycloalkoxy group may be further substituted by halogen), aryloxy, aralkyloxy, heteroaryloxy, heteroarylalkyloxy, aryl, heteroaryl, arylcarbamoyl, heteroarylcarbamoyl, arylalkylcarbamoyl, heteroarylalkylcarbamoyl, mono-lower alkylcarbamoyl, di-lower alkylcarbamoyl, lower alkylcarboxamide, arylcarboxamide, heteroarylcarboxamide, arylalkylcarboxamide, heteroarylalkylcarboxamide, alkanoyl, arylcarbonyl, arylalkylcarbonyl, alkylsulfonylamino, arylsulfonylamino, alkylaminosulfonyl, arylaminosulfonyl, aralkyl, alkanoylamino or alkanoylalkylamino; Y is CH or a nitrogen atom; —$X_2$ is a group represented by —$(CH_2)_n$—$NR_{G-4}R_{G-5}$, n is an integer of 2 to 4, where $R_{G-4}$ and $R_{G-5}$ taken together with a nitrogen atom together form a 5- to 8-membered monocyclic ring (this monocyclic ring may be substituted by a halogen atom, an oxo group, or a lower alkyl group of 1-3 carbon atoms which itself may be substituted by halogen, or where —$X_2$ is a group represented by

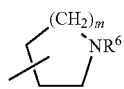

where m is an integer from 0 to 4, and $R_{G-6}$ is a lower alkyl or cycloalkyl group), or a pharmaceutically acceptable salt thereof. Such compounds, salts, and methods of preparing them are described in US Patent Publication No. 2005/0182045, published on Aug. 18, 2005, the contents of which are herein incorporated by reference. Compounds generally and specifically, and salts thereof, useful in the invention are further described therein. Specific compounds of interest are, 2-methyl-3-(4-(3-(pyrrolidin-1-yl)propoxy)phenyl)-5-(trifluoromethyl)quinazolin-4(3H)-one and 3-(4-(1-cyclobutylpiperidin-4-yloxy)phenyl)-2-methyl-5-(trifluoromethyl)quinazolin-4(3H)-one.

Other suitable histamine $H_3$ antagonists are, for example, compounds of formula:

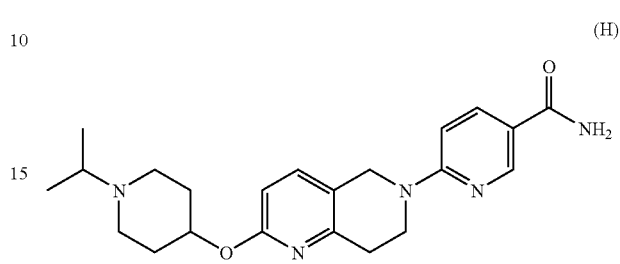

(H)

or 6-[2-(1-isopropylpiperidin-4-yloxy)-7,8-dihydro-5H-[1,6]naphthyridin-6-yl]nicotinamide and pharmaceutically acceptable salts thereof. Compounds, salts, and methods for their preparation are described in WO2007/052124, published May 10, 2007, the contents of which are herein incorporated by reference.

Other suitable histamine $H_3$ antagonists are, for example, compounds of formula:

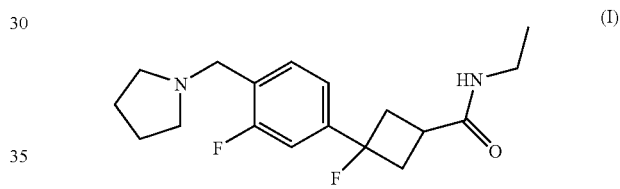

(I)

or N-ethyl-3-fluoro-3-(3-fluoro-4-(pyrrolidin-1-ylmethyl) phenyl)cyclobutanecarboxamide, and stereoisomeric forms of the compound. Stereoisomeric forms are (1r,3r)-N-ethyl-3-fluoro-3-(3-fluoro-4-(pyrrolidin-1-ylmethyl)phenyl)cyclobutanecarboxamide and trans-N-ethyl-3-fluoro-3-(3-fluoro-4-(pyrrolidin-1-ylmethyl)phenyl) cyclobutanecarboxamide. Such compounds and stereoisomeric forms are described in patent application US Patent Publication No. 2008/0176925, published Jul. 24, 2008, the contents of which are herein incorporated by reference.

Other suitable histamine $H_3$ antagonists are, for example, compounds of formula:

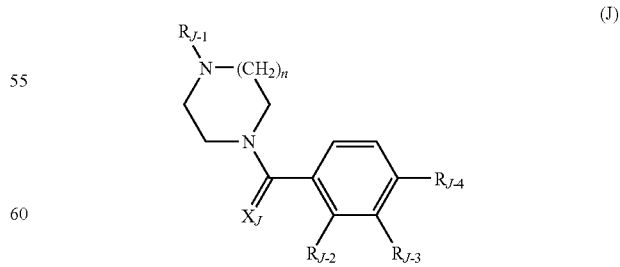

(J)

or a pharmaceutically acceptable salt thereof, wherein $R_1$ is $C_{1-10}$alkyl, $C_{3-8}$ alkenyl, $C_{3-8}$ cycloalkyl, ($C_{3-8}$ cycloalkyl)$C_{1-6}$ alkyl, ($C_{3-8}$ cycloalkyl)$C_{3-8}$ alkenyl, or ($C_{1-8}$ alkylcarbonyl)$C_{1-8}$ alkyl;

n is 1 or 2;

X$_J$ is O or S;

one of R$_2$, R$_3$ and R$_4$ is G and the other two independently are hydrogen, fluoro, chloro, bromo, nitro, trifluoromethyl, methyl, or C$_{1-3}$ alkoxy;

G is L$_J$Q$_J$;

L$_J$ is unbranched —(CH$_2$)$_{m3}$—, wherein m3 is an integer from 1 to 7;

Q$_J$ is NR$_8$R$_9$ wherein R$_8$ is independently selected from hydrogen, C$_{1-6}$ alkyl, C$_{3-6}$ alkenyl, 3-9 membered carbocyclyl, 3-12 membered heterocyclyl, phenyl, (6-9 membered heterocyclyl)C$_{1-6}$ alkylene, and (phenyl)C$_{1-6}$ alkylene; and R$_9$ is independently selected from C$_{1-6}$ alkyl, C$_{3-6}$ alkenyl, 6-9 membered carbocyclyl, 3-12 membered heterocyclyl, phenyl, (6-9-membered heteroyclyl)C$_{1-6}$ alkylene, and (phenyl)C$_{1-6}$ alkylene; or Q$_J$ is a saturated 3-12 membered N-linked heterocyclyl, wherein, in addition to the N-linking nitrogen, the 3-12 membered heterocyclyl may optionally contain between 1 and 3 additional heteroatoms independently selected from O, S, and NH; wherein Q is optionally substituted with 1-3 substituents independently selected from the group consisting of hydroxy, halo, carboxamide, C$_{1-6}$ alkyl, 5-9 membered or 6-9 membered heterocyclyl, —N(C$_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)C$_{1-3}$ alkylene, C$_{1-6}$ alkoxy, (C$_{3-6}$ cycloalkyl)-O—, phenyl, (phenyl)C$_{1-3}$ alkylene, and (phenyl)C$_{1-3}$ alkylene-O—, where each of above heterocyclyl, phenyl, and alkyl groups may be optionally substituted with from 1 to 3 substituents independently selected from trifluoromethyl, methoxy, halo, nitro, cyano, hydroxy, and C$_{1-3}$ alkyl; provided however that when R$_1$ is methyl, G is not piperidin-1-ylmethyl; and wherein each of the above alkyl, alkylene, alkenyl, heterocyclyl, cycloalkyl, carbocyclyl, and aryl groups may each be independently and optionally substituted with between 1 and 3 substituents independently selected from trifluoromethyl, methoxy, halo, amino, nitro, hydroxy, and C$_{1-3}$ alkyl. Such compounds, salts, and methods for preparing such compounds and salts are described in WO2004/037801, published May 6, 2004, the contents of which are herein incorporated by reference. Specific compounds of interest are ((4-isopropylpiperazin-1-yl) (4-(piperidin-1-ylmethyl)phenyl)methanone), (5-(3-cyclobutyl-2,3,4,5-tetrahydro-1H-benzo[d]azepin-7-yloxy)-N-methylpyrazine-2-carboxamide), as described in US2007/066821, published Mar. 22, 2007, the contents of which are herein incorporated by reference.

Other suitable histamine H$_3$ receptor antagonists are:

(K)

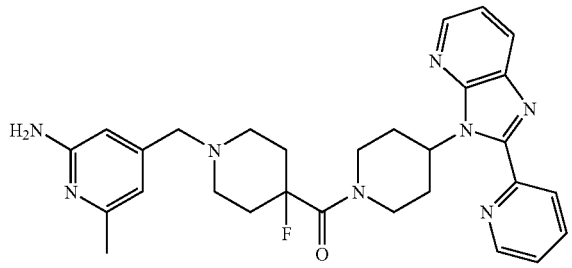

or (1-((2-amino-6-methylpyridin-4-yl)methyl)-4-fluoropiperidin-4-yl)(4-(2-(pyridin-2-yl)-3H-imidazo[4,5-b]pyridin-3-yl)piperidin-1-yl)methanone, or a pharmaceutically acceptable salt thereof. Such compounds, salts, and methods of preparing them are as described in patent application US Patent Publication No. 2007/0066644, published Mar. 22, 2007, the contents of which are herein incorporated by reference.

Another suitable histamine H$_3$ receptor antagonist is 3-[4-[(1-cyclobutyl-4-piperidinyl)-oxy]phenyl]-2-methyl-5-trifluoromethyl-4(3H)-quinazolinone, and salts thereof, which are described in WO2006/132424, published Dec. 14, 2006, the contents of which are herein incorporated by reference.

Another suitable histamine H$_3$ receptor antagonist is 2-methyl-3-[4-[3-(1-pyrrolidinyl)propoxy]phenyl]-5-trifluoromethyl-4(3H)-quinazolinone and salts thereof, which are described in WO2006/085692; published Aug. 17, 2006, and the related US Patent Publication No. 2008/0139589, published Jun. 12, 2008, as well as and WO2007/004735, published Aug. 17, 2006, and the related US Patent Publication No. 2009/0131664, published May 21, 2009, the contents of which are all incorporated by reference.

Other H$_3$ antagonist compounds are known, and are suitable for the treatment of osteoarthritis pain, including BF2649 (1-{3-[3-(4-chloro-phenyl)-propoxy]-propyl}-piperidine), 6-{4-[3-(r-2-methyl-pyrrolidin-1-yl)-propoxy]-phenyl}-2h-pyridazin-3-one, GSK-239512, PF-3654746, MK-0249, JNJ-17216498, CEP-26401, SCH-497079, ATH-90879, SAR-110894, APD916, S-38093, MK-3134, and JNJ-3100174. Another aspect of the invention relates to pharmaceutical compositions comprising the aforementioned compounds. Such compositions can be administered in accordance with a method of the invention, typically as part of a therapeutic regimen for treatment of the pain of osteoarthritis.

Another suitable histamine H$_3$ receptor antagonist is 1-(1-methylethyl)-4-{[4-(tetrahydro-2H-pyran-4-yloxy)phenyl]carbonyl}piperazine, or a pharmaceutically acceptable salt thereof, such the hydrochloride salt. This compound and salts are described in WO2009/030716, published Mar. 12, 2009, the contents of which are herein incorporated by reference.

Yet other H$_3$ antagonist compounds are known, and are suitable for the treatment of osteoarthritis pain, specifically those described in U.S. Pat. No. 7,153,889, issued Dec. 26, 2006; U.S. Pat. No. 7,205,316, issued Apr. 17, 2007; U.S. Pat. No. 7,098,222, issued Aug. 29, 2006; U.S. Pat. No. 7,358, 263, issued Apr. 15, 2008; U.S. Pat. No. 7,094,790, issued Aug. 22, 2006; U.S. Pat. No. 7,345,034, issued Mar. 18, 2008; WO2006/132914, published Dec. 14, 2006; US Patent Publication No. 2008/0027041, published Jan. 31, 2008; WO2004/101546, published Nov. 24, 2005; EP1595881, published Nov. 16, 2005; and US Patent Publication No. 2008/0096955, published Apr. 24, 2008, the contents of which are all incorporated by reference.

DETAILED DESCRIPTION OF THE INVENTION

Histamine H$_3$ Receptor Antagonists and Compositions Thereof

Histamine H$_3$ receptor antagonists of various structural classes have been identified. Histamine H$_3$ receptor antagonists have been identified as useful for treating various indications. However, the invention relates to the use of histamine H$_3$ antagonists for treating a particular indication, osteoarthritis pain. Many histamine H$_3$ receptor antagonists are reported in the literature.

Suitable histamine H$_3$ receptor antagonists are as described in the Summary of the Invention. Where the terms for describing the compound formulae are not explicitly defined, suitable definitions are described below in the Definition of Terms.

Particularly preferred compounds for the method include, but are not limited to, (S)-3-Hydroxy-1-[2-(3-piperidin-1-yl-cyclobutyl)-benzothiazol-6-yl]-pyrrolidin-2-one, Trans-2-[2-(3-piperidin-1-ylcyclobutyl)-1,3-benzothiazol-6-yl]pyridazin-3(2H)-one, Cis-2-[2-(3-piperidin-1-ylcyclobutyl)-1,3-benzothiazol-6-yl]pyridazin-3(2H)-one, (4-(2-(2-[2(R)-Methyl-1-pyrrolidinyl]ethyl)-1-benzofuran-5-yl) benzonitrile), (6-(3-Cyclobutyl-2,3,4,5-tetrahydro-1H-benzo[d]azepin-7-yloxy)-N-methyl-nicotinamide), (5-(3-cyclobutyl-2,3,4,5-tetrahydro-1H-benzo[d]azepin-7-yloxy)-N-methylpyrazine-2-carboxamide), 1-{6-[(3-cyclobutyl-2,3,4,5-tetrahydro-1H-3-benzazepin-7-yl)oxy]-3-pyridinyl}-2-pyrrolidinone, (4-isopropyl-1,4-diazepan-1-yl)(1-(6-(trifluoromethyl)pyridin-3-yl)piperidin-4-yl)methanone, 2-methyl-3-(4-(3-(pyrrolidin-1-yl)propoxy)phenyl)-5-(trifluoromethyl)quinazolin-4(3H)-one, 3-(4-(1-cyclobutylpiperidin-4-yloxy)phenyl)-2-methyl-5-(trifluoromethyl) quinazolin-4(3H)-one, 6-(2-(1-isopropylpiperidin-4-yloxy)-7,8-dihydro-1,6-naphthyridin-6(5H)-yl)nicotinamide, N-ethyl-3-fluoro-3-(3-fluoro-4-(pyrrolidin-1-ylmethyl)phenyl)cyclobutanecarboxamide, (1r,3r)-N-ethyl-3-fluoro-3-(3-fluoro-4-(pyrrolidin-1-ylmethyl)phenyl)cyclobutanecarboxamide, trans-N-ethyl-3-fluoro-3-(3-fluoro-4-(pyrrolidin-1-ylmethyl)phenyl)cyclobutanecarboxamide, ((4-isopropylpiperazin-1-yl)(4-(piperidin-1-ylmethyl)phenyl) methanone), (5-(3-cyclobutyl-2,3,4,5-tetrahydro-1H-benzo [d]azepin-7-yloxy)-N-methylpyrazine-2-carboxamide), (14 (2-amino-6-methylpyridin-4-yl)methyl)-4-fluoropiperidin-4-yl)(4-(2-(pyridin-2-yl)-3H-imidazo[4,5-b]pyridin-3-yl) piperidin-1-yl)methanone, and (1-{3-[3-(4-Chloro-phenyl)-propoxy]-propyl}-piperidine), 6-{4-[3-(r-2-methyl-pyrrolidin-1-yl)-propoxy]-phenyl}-2h-pyridazin-3-one, 1-(1-methylethyl)-4-{[4-(tetrahydro-2H-pyran-4-yloxy) phenyl]carbonyl}piperazine.

More particularly preferred compounds include, but are not limited to, Cis-2-[2-(3-piperidin-1-ylcyclobutyl)-1,3-benzothiazol-6-yl]pyridazin-3(2H)-one, Trans-2-[2-(3-piperidin-1-ylcyclobutyl)-1,3-benzothiazol-6-yl]pyridazin-3 (2H)-one, (S)-3-Hydroxy-1-[2-(3-piperidin-1-yl-cyclobutyl)-benzothiazol-6-yl]-pyrrolidin-2-one, (4-(2-(2-[2 (R)-Methyl-1-pyrrolidinyl]ethyl)-1-benzofuran-5-yl) benzonitrile), (6-(3-Cyclobutyl-2,3,4,5-tetrahydro-1H-benzo[d]azepin-7-yloxy)-N-methyl-nicotinamide), (5-(3-cyclobutyl-2,3,4,5-tetrahydro-1H-benzo[d]azepin-7-yloxy)-N-methylpyrazine-2-carboxamide), (4-isopropyl-1,4-diazepan-1-yl)(1-(6-(trifluoromethyl)pyridin-3-yl) piperidin-4-yl)methanone.

DEFINITION OF TERMS

Unless otherwise defined, terms as used in the specification refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylene" means a divalent group derived from a straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means a —$NH_2$ group.

The term "aryl" as used herein means a monocyclic hydrocarbon aromatic ring system. Representative examples of aryl include, but are not limited to, phenyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkylcarbonyl, formyl, haloalkoxy, haloalkyl, halogen, hydroxy, hydroxyalkyl, mercapto, nitro, thioalkoxy, $NR_AR_B$, and ($NR_AR_B$)sulfonyl.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(═O)— group.

The term "carboxy" as used herein means a —$CO_2H$ group, which may be protected as an ester group —$CO_2$-alkyl.

The term "cyano" as used herein means a —CN group.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of the invention are substituted with 0, 1, 2, 3, or 4 substituents selected from acyl, acyloxy, alkenyl, alkoxy, alkoxyalkoxy, alkoxyalkyl, alkoxycarbonyl, alkoxyimino, alkyl, alkynyl, amido, carboxy, cyano, ethylenedioxy, formyl, haloalkoxy, haloalkyl, halogen, hydroxy, hydroxyalkyl, methylenedioxy, oxo, thioalkoxy, and —$NR_AR_B$.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkoxy" as used herein means at least one fluoroalkyl group, as defined herein, appended to the parent molecular moiety through an oxygen group, as defined herein. Representative examples of fluoroalkyl include, but are not limited to, trifluoromethoxy ($CF_3O$), and difluoromethoxy ($CHF_2O$).

The term "fluoroalkyl" as used herein means at least one fluoro group, as defined herein, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy group, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, refers to an aromatic ring containing one or more heteroatoms independently selected from nitrogen, oxygen, or sulfur, or a tautomer thereof. Such rings can be monocyclic or bicyclic as further described herein. Heteroaryl rings are connected to the parent molecular moiety, or to $L_2$ or $L_3$, wherein $L_2$ and $L_3$ are defined in formula (I), through a carbon or nitrogen atom.

The terms "monocyclic heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or atom; one, two, or three N atoms arranged in a suitable manner to provide an aromatic ring; or a ring wherein two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five membered rings containing one to four nitrogen atoms; and five membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,3]oxadiazolyl, thiazolyl, thienyl, [1,2,3]triazinyl, [1,2,4]triazinyl, [1,3,5]triazinyl, [1,2,3]triazolyl, and [1,2,4]triazolyl.

The term "bicyclic heteroaryl" or "8- to 12-membered bicyclic heteroaryl ring", as used herein, refers to an 8-, 9-, 10-, 11-, or 12-membered bicyclic aromatic ring containing at least 3 double bonds, and wherein the atoms of the ring include one or more heteroatoms independently selected from oxygen, sulfur, and nitrogen. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, thieno[3,2-b]pyridinyl, and pyrrolopyrimidinyl.

Heteroaryl groups of the invention, whether monocyclic or bicyclic, may be substituted with hydrogen, or optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_AR_B$, and ($NR_AR_B$)carbonyl. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the present invention may be present as tautomers.

The terms "heterocyclic ring" and "heterocycle", as used herein, refer to a 4- to 12-membered monocyclic or bicyclic ring containing one, two, three, four, or five heteroatoms independently selected from the group consisting of nitrogen, oxygen, and sulfur and also containing either at least one carbon atom attached to four other atoms or one carbon atom substituted with an oxo group and attached to two other atoms. Four- and five-membered rings may have zero or one double bond. Six-membered rings may have zero, one, or two double bonds. Seven- and eight-membered rings may have zero, one, two, or three double bonds. The non-aromatic heterocycle groups of the invention can be attached through a carbon atom or a nitrogen atom. The non-aromatic heterocycle groups may be present in tautomeric form. Representative examples of nitrogen-containing heterocycles include, but are not limited to, azepanyl, azetidinyl, aziridinyl, azocanyl, dihydropyridazinyl, dihydropyridinyl, dihydropyrimidinyl, morpholinyl, piperazinyl, piperidinyl, pyrrolidinyl, pyrrolinyl, dihydrothiazolyl, dihydropyridinyl, and thiomorpholinyl. Representative examples of non-nitrogen containing non-aromatic heterocycles include, but are not limited to, dioxanyl, dithianyl, tetrahydrofuryl, dihydropyranyl, tetrahydropyranyl, and [1,3]dioxolanyl.

The heterocycles of the invention are substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, amido, arylalkyl, arylalkoxycarbonyl, carboxy, cyano, formyl, haloalkoxy, haloalkyl, halogen, hydroxy, hydroxyalkyl, mercapto, nitro, oxo, thioalkoxy, —$NR_AR_B$, and ($NR_AR_B$)sulfonyl.

Additional examples of heterocycles include, but are not limited to, azetidin-2-one, azepan-2-one, isoindolin-1,3-dione, (Z)-1H-benzo[e][1,4]diazepin-5(4H)-one, pyridazin-3(2H)-one, pyridin-2(1H)-one, pyrimidin-2(1H)-one, pyrimidin-2,4(1H,3H)-dione, pyrrolidin-2-one, benzo[d]thiazol-2(3H)-one, pyridin-4(1H)-one, imidazolidin-2-one, 1H-imidazol-2(3H)-one, piperidin-2-one, tetrahydropyrimidin-2(1H)-one, 1H-benzo[d]imidazol-2(3H)-one, [1,2,4]thiadiazolonyl, [1,2,5]thiadiazolonyl, [1,3,4]thiadiazinonyl, [1,2,4]oxadiazolonyl, [1,2,5]oxadiazolonyl, [1,3,4]oxadiazinonyl, and 1,5-dihydro-benzo[b][1,4]diazepin-2-on-yl.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl trifilate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "—$NR_AR_B$" as used herein means two groups, $R_A$ and $R_B$, which are appended to the parent molecular moiety through a nitrogen atom. $R_A$ and $R_B$ are independently selected from hydrogen, alkyl, acyl, and formyl. Representative examples of —$NR_AR_B$ include, but are not limited to, amino, dimethylamino, methylamino, acetylamino, and acetylmethylamino.

The term "($NR_AR_B$)alkyl" as used herein means an —$NR_AR_B$ group, as defined herein, appended to the parent molecular moiety through an alkyl group, as defined herein. Representative examples of ($NR_AR_B$)alkyl include, but are not limited to, 2-(methylamino)ethyl, 2-(dimethylamino)ethyl, 2-(amino)ethyl, 2-(ethylmethylamino)ethyl, and the like.

The term "($NR_AR_B$)carbonyl" as used herein means an —$NR_AR_B$ group, as defined herein, appended to the parent molecular moiety through a carbonyl group, as defined herein. Representative examples of ($NR_AR_B$)carbonyl include, but are not limited to, aminocarbonyl, (methylamino)carbonyl, (dimethylamino)carbonyl, (ethylmethylamino)carbonyl, and the like.

The term "($NR_AR_B$)sulfonyl" as used herein means a —$NR_AR_B$ group, as defined herein, appended to the parent molecular moiety through a sulfonyl group, as defined herein. Representative examples of ($NR_AR_B$)sulfonyl include, but are not limited to, aminosulfonyl, (methylamino)sulfonyl, (dimethylamino)sulfonyl and (ethylmethylamino)sulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl trifilate, a dialkyl anhydride, for example as represented by (alkyl-O)$_2$C=O, a diaryl anhydride, for example as represented by (aryl-O)$_2$C=O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —S(O)$_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

The compounds of the invention can be used in the form of pharmaceutically acceptable salts derived from inorganic or organic acids. The term "pharmaceutically acceptable salts", as used herein, refer to acid addition salts, carboxylate salts, amino acid addition salts, and zwitterion salts of compounds of formulae (A), (B), (C), (D), (E), (F), (G), (H), (I), (J), or (K) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable acid. Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, proprionic, hydrobromic, glucuronic, methanesulfonic, ethanesulfonic, naphthylene sulfonic, lactic, fumaric, oxalic, and succinic acid.

The aforementioned histamine H$_3$ antagonist antagonists may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Histamine H$_3$ receptor antagonists may exist as cis or trans isomers, wherein substituents on a ring may attached in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

Compositions comprising a therapeutically effective amount of a compound of formulae (A), (B), (C), (D), (E), (F), (G), (H), (I), (J), or (K) in combination with a pharmaceutically acceptable carrier also are suitable for the method. The compositions comprise the histamine H$_3$ receptor antagonist formulated together with one or more non-toxic pharmaceutically acceptable carriers. The pharmaceutical compositions can be formulated for oral administration in solid or liquid form, for parenteral intravenous, subcutaneous, intramuscular, intraperitoneal, intra-arterial, or intradermal injection, for or for vaginal, nasal, topical, or rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

Administering the Histamine H$_3$ Receptor Antagonist

Histamine H$_3$ receptor antagonists are compounds which block activation of the histamine H$_3$ receptor. The histamine H$_3$ receptor antagonist compounds and compositions of the invention can be used for treating and preventing osteoarthritis pain in a mammal. The compound, including salts thereof, or a composition can be administered for treatment of osteoarthritis pain. The histamine-3 receptor antagonist can be administered, either alone or in combination with another active agent, for example, as part of a therapeutic regimen.

For example, the invention provides for a method of treating osteoarthritis to a mammal requiring treatment, comprising administering to the mammal an effective amount of ibuprofen, celecoxib, or rofecoxib and an effective amount of a histamine H$_3$ receptor antagonist, or a pharmaceutically acceptable salt thereof.

The pharmaceutical compositions can be formulated for oral administration in solid or liquid form, for parenteral intravenous, subcutaneous, intramuscular, intraperitoneal, intra-arterial, or intradermal injection, for or for vaginal, nasal, topical, or rectal administration.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The pharmaceutical compositions of this invention can be administered to humans and other mammals by oral administration or by injection, including by intravenous, subcutaneous, intramuscular, intraperitoneal, intra-arterial, and intradermal injection. The pharmaceutical compositions of this invention can be administered to humans and other mammals topically (as by powders, lotions, ointments or drops applied to the skin), bucally, or inhaled, as an oral or nasal spray. The pharmaceutical compositions of this invention can be administered to humans and other mammals intrarectally, intravaginally. The term "parenterally," as used herein, refers to modes of administration, which include intravenous, intramuscular, intraperitoneal, intrasternal, subcutaneous and intraarticular.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of formula (A) administered to a human or lower animal may range from about 0.0003 to about 30 mg/kg of body weight. For purposes of oral administration, more preferable doses can be in the range of from about 0.0003 to about 1 mg/kg body weight. If desired, the effective daily dose can be divided into multiple doses for purposes of administration; consequently, single dose compositions may contain such amounts or submultiples thereof to make up the daily dose.

For treatment or prevention of disease, the total daily dose of the compounds of formula (B) administered to a human or lower animal may range from about 0.001 to about 30 mg/kg of body weight. For purposes of oral administration, more preferable doses can be in the range of from about 0.001 to about 1 mg/kg body weight. If desired, the effective daily dose can be divided into multiple doses for purposes of administration; consequently, single dose compositions may contain such amounts or submultiples thereof to make up the daily dose.

For treatment or prevention of disease, the total daily dose of the compounds of formula (C) administered to a human or lower animal may range from about 0.003 to about 30 mg/kg of body weight. For purposes of oral administration, more preferable doses can be in the range of from about 0.1 to about 15 mg/kg body weight. If desired, the effective daily dose can be divided into multiple doses for purposes of administration; consequently, single dose compositions may contain such amounts or submultiples thereof to make up the daily dose.

Compositions having compounds of formula (D) may contain from 0.1% to 99% by weight, preferably from 10 to 60%, by weight, of the active material, depending on the method of administration. The dose of the compound used in treatment will vary. However, as a general guide suitable unit doses for compounds of formula (D) may be 0.05 to 1000 mg, more suitably 1.0 to 200 mg, and such unit doses may be administered more than once a day, for example two or three a day. Such therapy may extend for a number of weeks or months.

Compositions having compound of structure (E) may be prepared according to methods described in WO2008/104590, published Sep. 4, 2008, the contents of which are herein incorporated by reference.

Compositions having compounds of formula (F) may contain from 0.1% to 99% by weight, preferably from 10 to 60%, by weight, of the active material, depending on the method of administration. The dose of the compound used in treatment will vary. However, as a general guide suitable unit doses for compounds of formula (F) may be 0.05 to 1000 mg, more suitably 1.0 to 200 mg, and such unit doses may be administered more than once a day, for example two or three a day. Such therapy may extend for a number of weeks or months.

Compositions having compound of structure (G) may be prepared according to methods described in WO2005/018045, published Aug. 18, 2005, the contents of which are herein incorporated by reference.

Suitable methods for administering a compound of structure (H) may be prepared according to methods described in WO2007/052124, published May 10, 2007, the contents of which are herein incorporated by reference.

Suitable methods for administering a compound of structure (I) may be prepared according to methods described in US Patent Publication No. 2008/0176925, published Jul. 24, 2008, the contents of which are herein incorporated by reference.

The daily dosage of products having a compound of formula (J) may be varied over a wide range from 1 to 1,000 mg per adult human per day. For oral administration, the compositions having a compound of formula (J) are preferably provided in the form of tablets containing 1.0, 5.0, 10.0, 15.0, 25.0, 50.0, 100, 250, and 500 milligrams of the active ingredient for the symptomatic adjustment of the dosage to the subject to be treated. An effective amount of the drug is oridinarily supplied at a dosage level of from about 0.01 mg/kg to about 10 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Suitable methods for administering a compound of structure (K) may be prepared according to methods described in US Patent Publication No. 2007/0066644, published Mar. 22, 2007, the contents of which are herein incorporated by reference.

Optimal dosages to be administered may be readily determined by those skilled in the art, and will vary with the particular compound used, the mod of administration, the strength of the preparation, the mode of administration, and the advancement of the disease condition. In addition, factors associated with the particular patient being treated, including patient age, weight, diet, and time of administration can result in the need to adjust dosages.

Methods for Preparing Assayed Compounds

Suitable histamine $H_3$ receptor antagonists for the invention can be prepared in the aforementioned patent literature references. The following example compounds illustrate the preparation of some of the histamine $H_3$ antagonists for use in osteoarthritis pain therapy.

EXAMPLES

Example 1

Cis-2-[2-(3-piperidin-1-ylcyclobutyl)-1,3-benzothiazol-6-yl]pyridazin-3(2H)-one

Preparation of the Compound is Described in US Patent Publication No. 20070066588(A1). The title compound was prepared according to the procedures described therein. Compound was an off-white solid, mp 127-128° C. $^1$H NMR (400 MHz, CDCl$_3$). δ ppm 8.14 (t, J=2.61 Hz, 1H) 8.02 (d, J=8.59 Hz, 1H) 7.92 (dd, J=3.68, 1.53 Hz, 1H) 7.66-7.70 (m, 1H) 7.23-7.30 (m, 1H) 7.08 (dd, J=9.36, 1.69 Hz, 1H) 3.52-3.65 (m, 1H) 2.75-2.86 (m, 1H) 2.62-2.73 (m, 2H) 2.25-2.41 (m, 6H) 1.55-1.66 (m, 4H) 1.41-1.52 (m, 2H). MS: (M+H)$^+$=367.

Example 2

Trans-2-[2-(3-piperidin-1-ylcyclobutyl)-1,3-benzothiazol-6-yl]pyridazin-3(2H)-one Preparation of this Compound is Described in US Patent Publication No. 20070066588(A1). The title compound was prepared according to the procedures described therein. $^1$H NMR (500 MHz, CDCl$_3$) δ ppm 8.15 (d, J=2.14 Hz, 1H) 8.05 (d, J=8.85 Hz, 1H) 7.93 (dd, J=3.81, 1.68 Hz, 1H) 7.70 (dd, J=8.85, 2.14 Hz, 1H) 7.24-7.31 (m, 1H) 7.09 (dd, J=9.46, 1.83 Hz, 1H) 3.80-3.92 (m, 1H) 3.10-3.19 (m, 1H) 2.53-2.70 (m, 4H) 2.21-2.47 (m, 4H) 1.58-1.72 (m, 4H) 1.42-1.55 (m, 2H). MS: (M+H)$^+$=367.

Example 3

(S)-3-Hydroxy-1-[2-(3-piperidin-1-yl-cyclobutyl)-benzothiazol-6-yl]-pyrrolidin-2-one To a microwave vial equipped with magnetic stir bar, 50 mg (0.14 mmol) of 6-bromo-2-[trans-3-(1-piperidinyl)cyclobutyl]benzothiazole (prepared as described in Cowart, et al. Benzothiazole cyclobutylamine derivatives, US Patent Publication No. 2007/0066588(A1)) was added, followed by (S)-3-hydroxypyrrolidin-2-one (50 mg, 0.50 mmol), Pd$_2$(dba)$_3$ (4.0 mg, 0.0044 mmol), xantphos (6.9 mg, 0.012 mmol) and Cs$_2$CO$_3$ (68 mg, 0.21 mmol). The reaction vial was sealed with an aluminum cap, and purged with N$_2$, then dioxane (2 mL) was introduced via a syringe. The reaction mixture was then heated in a microwave oven at 150° C. for 60 minutes. The reaction mixture was cooled to room temperature, filtered, and the solvent was removed under vacuum, after which the residue was purified via chromatography on silica gel, eluting with a gradient of 0-10% methanol in dichloromethane, to give the desired product (21 mg, 40%). $^1$H NMR (300 MHz) δ 8.34 (d, J=2.2, 1H), 7.97 (d, J=8.9, 1H), 7.61 (dd, J=2.2, 8.9, 1H), 4.51 (dd, J=8.2, 9.7, 1H), 3.86 (m, 3H), 3.13 (m, 1H), 2.66 (m, 1H), 2.58 (m, 4H), 2.32 (m, 3H), 2.15 (ddd, J=9.5, 12.6, 19.1, 1H), 1.61 (m, 6H), 1.48 (m, 2H). MS (ESI) m/z=372.0 (M+H)$^+$ Example 4

(4-(2-(2-[2(R)-Methyl-1-pyrrolidinyl]ethyl)-1-benzofuran-5-yl)benzonitrile)

Preparation of this compound is described in U.S. Pat. No. 6,969,730(B2). The title compound was prepared according to the procedures described therein. ¹H NMR (300 MHz, CD₃OD). δ 7.88 (m, 1H), 7.71 (m, 4H), 7.50 (m, 2H), 6.82 (s, 1H), 3.72-3.9 (m, 2H), 3.58 (m, 1H), 3.25-3.5 (m, 4H), 2.48 (m, 1H), 2.05-2.2 (m, 2H), 1.75 (m, 1H), 1.50 (d, J=6 Hz, 3H); MS (DCI) m/z 331 (M+H)⁺. The free base was converted to a pharmaceutically acceptable salt, the phosphate salt as follows: 20 grams of free base 4-(2-(2-[2(R)-Methyl-1-pyrrolidinyl]ethyl)-1-benzofuran-5-yl)benzonitrile was dissolved in 35 mL of 95:5 methanol/water at reflux, and 4.79 g of phosphoric acid was added dropwise. On cooling a white powder was deposited, which was collected by filtration and dried to give 15.1 grams of the monophosphate salt, 4-(2-(2-[2(R)-methyl-1-pyrrolidinyl]ethyl)-1-benzofuran-5-yl)benzonitrile phosphate, m.p. 203-204. Combustion analysis, calculated for $C_{22}H_{22}N_2O.H_3PO_4$ was C, 61.68%; H, 5.88%; N, 6.54%. Found. C, 61.30%; H, 5.66%; N, 6.39%.

Example 5

(6-(3-Cyclobutyl-2,3,4,5-tetrahydro-1H-benzo[d]azepin-7-yloxy)-N-methyl-nicotinamide)

Preparation of this Compound is Described in US Patent Publication No. 20070299056(A1). The title compound was prepared according to the procedures described therein. ¹H NMR (300 MHz) δ 8.56 (d, J=2.1, 1H), 8.47 (q, J=4.1, 1H), 8.19 (dd, J=2.5, 8.6, 1H), 7.15 (d, J=8.1, 1H), 7.03 (d, J=8.5, 1H), 6.91 (d, J=2.5, 1H), 6.86 (dd, J=2.5, 8.0, 1H), 2.83 (m, 4H), 2.78 (m, 4H), 2.37 (m, 4H), 1.99 (m, 2H), 1.78 (m, 2H), 1.60 (m, 2H). MS (ESI) m/z=352.1 (M+H)⁺.

Example 6

(5-(3-cyclobutyl-2,3,4,5-tetrahydro-1H-benzo[d]azepin-7-yloxy)-N-methylpyrazine-2-carboxamide)

Preparation of this Compound is Described in US Patent Publication No. 20070299056(A1). The title compound was prepared according to the procedures described therein. ¹H NMR (300 MHz, CDCL3) δ 8.90 (d, J=1.3, 1H), 8.26 (d, J=1.3, 1H), 7.61 (br s, 1H), 7.15 (d, J=8.8, 1H), 6.90 (m, 2H), 3.03 (d, J=5.1, 3H), 2.93 (m, 4H), 2.79 (dd, J=8.1, 16.2, 1H), 2.47 (m, 4H), 2.14-2.01 (m, 2H), 1.99-1.82 (m, 2H), 1.77-1.60 (m, 2H). MS (ESI) m/z=353.0 (M+H)⁺. CHN: Found C, 68.09; H, 6.73; N, 15.74; Theory C, 68.16; H, 6.86; N, 15.90.

Example 7

(4-isopropyl-1,4-diazepan-1-yl)(1-(6-(trifluoromethyl)pyridin-3-yl)piperidin-4-yl)methanone Preparation of this compound is described in WO2004/101546(A1). The title compound was prepared according to the procedures described therein. ¹H NMR (300 MHz, CHLOROFORM-D) δ ppm 1.00 (dd, J=6.54, 4.56 Hz, 6H) 1.73-1.91 (m, 4H) 2.00 (dd, J=13.29, 1.78 Hz, 2H) 2.54-2.75 (m, 5H) 2.87-3.01 (m, 3H) 3.51-3.66 (m, 4H) 3.87 (d, J=12.69 Hz, 2H) 7.19 (dd, J=8.92, 2.97 Hz, 1H) 7.50 (d, J=9.12 Hz, 1H) 8.34 (d, J=2.78 Hz, 1H). MS (DCI—NH₃) m/z 399 (M+H)⁺.

Example 8

2-[4-((1S,2S)-2-{[(2S)-2-methylpyrrolidin-1-yl]methyl}cyclopropyl)phenyl]pyridazin-3(2H)-one Preparation of this compound is described in US2008/0242653(A1). The title compound was prepared according to the procedures described therein, for example as described below.

Example 8A (E)-3-(4-bromophenyl)prop-2-en-1-ol

To a solution of (E)-ethyl 3-(4-bromophenyl)acrylate (25 g, 96 mmol) in DCM (300 ml) under nitrogen and cooled to −78° C. was added dropwise DIBAL-H (240 ml, 1M in DCM, 240 mmol) in about 20 minutes. The mixture was stirred at −78° C. for 2 hours. Then, the dry ice bath was removed. The reaction was diluted with DCM (500 mL), quenched with HCl (1N), and partitioned. The combined organic phases were washed with H₂O, dried and concentrated under reduced pressure to provide the title compound. ¹H NMR (300 MHz, CDCl₃): δ 1.43 (t, J=6 Hz, 1H), 4.32 (t, J=4.5 Hz, 2H), 6.37 (dt, J=16.5 Hz, J=6 Hz, 1H), 6.57 (d, J=15 Hz, 1H), 7.25 (d, J=9 Hz, 2H), 7.45 (d, J=9 Hz, 2H). MS (DCI—NH₃) m/z 214 (M+H)⁺.

Example 8B 2-butyl-1,3,6,2-dioxazaborocane

To a solution of 2,2'-azanediyldiethanol (26.12 g, 246 mmol) in DCM (250 ml) and ether (500 mL) was added n-butylboronic acid (25.4 g, 242 mmol) and molecular sieves (3 A, 4-6 mesh, 65 g). It was stirred at ambient temperature for 2 hours. The mixture was filtered, and the filtrate was concentrated under reduced pressure. The resulting white solid was recrystallized with DCM/ether to provide white crystals as the title product. NMR (300 MHz, CDCl₃): δ 0.47 (t, J=9 Hz, 2H), 0.88 (t, J=6 Hz, 3H), 1.20-1.37 (m, 4H), 2.82 (br, 2H), 3.24 (br, 2H), 3.95 (br, 4H), 4.27 (br, 1H). MS (DCI—NH₃) m/z 172 (M+H)⁺.

Example 8C (4R,5R)-2-butyl-N4,N4,N5,N5-tetramethyl-1,3,2-dioxaborolane-4,5-dicarboxamide A solution of the product from Example 8B (31.3 g, 183 mmol) and (2R,3R)-2,3-dihydroxy-N1,N1,N4,N4-tetramethylsuccinamide (31 g, 149 mmol) in DCM (600 mL) was treated with brine (120 mL) and stirred at ambient temperature for 30 minutes. The organic layer was separated, and the aqueous layer was extracted with additional DCM. The organic layers were combined and washed with brine (700 mL), dried with MgSO₄, and concentrated under reduced pressure to provide the title product. NMR (300 MHz, CDCl₃): δ 0.83-0.90 (m, 6H), 1.26-1.42 (m, 5H), 2.98 (s, 6H), 3.20 (s, 6H). MS (DCI—NH₃) m/z 205 (M+H)⁺.

Example 8D (1S,2S)-[2-(4-Bromophenyl)cyclopropyl]methanol

A solution of DME (24.39 mL, 235 mmol) in DCM (700 mL) under nitrogen atmosphere was cooled to −10° C., and diethylzinc (235 mL, 1M in hexane, 235 mmol) was added over 5-10 minutes followed by diiodomethane (37.9 mL, 469 mmol). The product from Example 8C (33.0 g, 122 mmol) in 100 mL DCM was added in 5-10 minutes. The temperature was maintained from −5° to −10° C. throughout the additions. The product from Example 8A, (E)-3-(4-bromophenyl)prop-2-en-1-ol (20 g, 94 mmol) in DCM (150 mL) was added dropwise, and the reaction mixture was stirred at ambient temperature for 16 hours. It was quenched with saturated aqueous $NH_4Cl$ (300 mL), HCl (1N, 480 mL) and diluted with ether (900 mL). The organic layer was separated. The aqueous layer was extracted with additional ether. The organic layers were combined and treated with NaOH (2N, 880 mL). To the solution, $H_2O_2$ (30%, 136 mL) was added dropwise while the reaction was cooled with an ice bath. The solution was stirred for 5-10 minutes. The organic layer was separated, washed with HCl (1N), saturated aqueous $Na_2S_2O_3$, saturated aqueous $NaHCO_3$, and brine, dried and concentrated. The residue was chromatographed on silica gel eluting with 5-15% EtOAc/Hexane to provide the title compound. $^1$H NMR (300 MHz, $CDCl_3$): δ 0.92-1.0 (m, 2H), 1.45-1.48 (m, 2H), 1.76-1.85 (m, 1H), 3.61 (d, J=7.5 Hz, 2H), 6.95 (d, J=9 Hz, 2H), 7.37 (d, J=9 Hz, 2H). MS (DCI—$NH_3$) m/z 228 (M+H)$^+$. (ee 94%).

Example 8E (1S,2S)-2-(4-Bromophenyl)cyclopropanecarbaldehyde

To a solution of oxalyl chloride (17.50 mL, 2 M in DCM, 35.0 mmol) in DCM (150 mL) under nitrogen atmosphere and cooled to −78° C. was added dro wise DMSO (4.97 mL, 70.0 mmol), followed with the dropwise addition of a solution of the product from Example 8D, ((1S,2S)-2-(4-bromophenyl)cyclopropyl)methanol (5.3 g, 23.34 mmol) in DCM (100 mL). The mixture was stirred 30 minutes at −78° C. Then the mixture was treated with triethylamine (13.01 mL, 93 mmol), and then the reaction temperature was raised to ambient temperature. The mixture was partitioned between DCM (400 mL) and $H_2O$ (400 mL). The organic layer was separated, washed with water, dried and concentrated under reduced pressure to provide the title product. $^1$H NMR (300 MHz, $CDCl_3$): δ 1.48 (m, 1H), 1.65 (dt, J=9 Hz, J=6 Hz, 1H), 2.15 (m, 1H), 2.57 (m, 1H), 6.98 (d, J=9 Hz, 2H), 7.45 (d, J=9 Hz, 2H), 9.46 (d, J=4.5 Hz, 1H). MS (DCI—$NH_3$) m/z 226 (M+H)$^+$.

Example 8F

1-{[(1S,2S)-2-(4-bromophenyl)cyclopropyl]methyl}-(2S)-2-methylpyrrolidine

A solution of the product from Example 8E, (1S,2S)-2-(4-bromophenyl)cyclopropanecarbaldehyde (5.7 g, 25.3 mmol) in DCM (20 ml) and MeOH (300 mL) was treated with (S)-2-methylpyrrolidine tartrate (8.94 g, 38.0 mmol) at ambient temperature, and the mixture was stirred for 5-10 minutes. Then, the mixture was cooled to 0° C., and a solution of $NaCNBH_3$ (2.51 g, 38.0 mmol) in MeOH (50 mL) was added dropwise. After addition, the reaction mixture was raised to room temperature and stirred overnight. The reaction mixture was treated with NaOH (1N) till basic, extracted with DCM thrice (500 mL×3), dried and concentrated under reduced pressure. The crude product was loaded onto a silica gel column and eluted with 1% to 3% methanol (containing 10% concentrated $NH_4OH$) in dichloromethane to provide the title product. $^1$H NMR (300 MHz, $CDCl_3$): δ 0.87-0.92 (m, 1H), 0.97-1.02 (m, 1H), 1.16 (d, J=6 Hz, 2H), 1.22 (m, 1H), 1.39-1.49 (m, 1H), 1.73-1.81 (m, 3H), 2.0 (m, 2H), 2.36 (q, J=6 Hz, 1H), 2.45 (m, 1H), 3.13 (dd, J=12 Hz, J=6 Hz, 1H), 3.25 (m, 1H), 7.00 (d, J=6 Hz, 2H), 7.37 (d, J=6 Hz, 2H). MS (DCI—$NH_3$) m/z 294 (M+H)$^+$.

Example 8G

2-[4-((1S,2S)-2-{[(2S)-2-Methylpyrrolidin-1-yl] methyl}cyclopropyl)phenyl]pyridazin-3(2H)-one A solution of the product from Example 8F, 1-{[(1S,2S)-2-(4-bromophenyl)cyclopropyl]methyl}-(2S)-2-methylpyrrolidine (100 mg, 0.340 mmol), pyridazin-3(2H)-one (52.3 mg, 0.544 mmol), N1,N2-dimethylethane-1,2-diamine (0.088 mL, 0.816 mmol) and copper(I) iodide (78 mg, 0.408 mmol) in pyridine (2 mL) under a nitrogen atmosphere in a sealed vial was heated in an oil bath to 135° C. for 16 hours. The reaction mixture was cooled and diluted with DCM (10 mL), filtered through diatomaceous earth and washed with DCM. The filtrate was washed sequentially with $H_2O$, 28-30% $NH_4OH$ (10 mL×2), and $H_2O$, dried with $MgSO_4$ and concentrated under reduced pressure. The residue was chromatographed on silica gel eluting with concentrated concentrated $NH_4OH/MeOH/DCM$ (0.4/4/96) to provide the title compound. $^1$H NMR (300 MHz, $CD_3OD$) δ 0.90-0.97 (m, 1H), 1.03-1.09 (m, 1H), 1.15 (d, J=6 Hz, 3H), 1.23-1.33 (m, 1H), 1.39-1.49 (m, 1H), 1.70-1.80 (m, 2H), 1.82-2.05 (m, 3H), 2.26-2.42 (m, 2H), 3.16 (dd, J=12 Hz, J=6 Hz, 1H), 3.21-3.28 (m, 1H), 7.07 (d, J=6 Hz, 2H), 7.21 (dd, J=6 Hz, J=1.5 Hz, 2H), 7.43 (d, J=6 Hz, 2H), 7.47 (dd, J=9 Hz, J=3 Hz, 1H), 8.02 (dd, J=6 Hz, J=1.5 Hz, 1H). MS (DCI—$NH_3$) m/z 310 (M+H)$^+$.

Example 8H

2-[4-((1S,2S)-2-{[(2S)-2-Methylpyrrolidin-1-yl] methyl}cyclopropyl)phenyl]pyridazin-3(2H)-one (2R,3R)-2,3-dihydroxysuccinate A solution of the product from Example 8G (3.25 g, 10.5 mmol) in methanol (20 mL) was treated with L-tartaric acid (1.577 g, 10.5 mmol) and stirred at ambient temperature for 1 hour. The mixture was concentrated under reduced pressure, and the resulting solid was recrystallized from isopropyl alcohol/acetone to provide the titled compound as the L-tartrate. $^1$H NMR (300 MHz, $CD_3OD$) δ 1.12-1.19 (m, 1H), 1.23-1.30 (m, 1H), 1.43 (d, J=6 Hz, 3H), 1.47-1.56 (m, 1H), 1.72-1.81 (m, 1H), 2.02-2.19 (m, 3H), 2.28-2.39 (m, 1H), 3.04-3.11 (m, 1H), 3.43-3.55 (m, 2H), 3.64-3.75 (m, 1H), 4.38 (s, 2H), 7.08 (dd, J=6 Hz, J=2 Hz, 1H), 7.28 (d, J=6 Hz, 2H), 7.44-7.50 (m, 3H), 8.03 (m, 1H). MS (DCI—$NH_3$) m/z 310 (M+H)$^+$. Anal. Calcd. for $C_{23}H_{29}N_3O_7$: C, 60.12; 6.36; N, 9.14. Found. 60.07; 5.76; N, 8.82.

Determination of Efficacy in Blockade of Osteoarthritis Pain

Histamine $H_3$ antagonists of the classes described were found to be effective in osteoarthritis pain. This model, the MIA-OA model is well known to those skilled in the art. A general review of various models of pain is found in Joshi and Honore, Expert Opinion in Drug Discovery (2004) 1, pp. 323-334, and in the book 'Drug Discovery and Evaluation, $2^{nd}$ edition' (H. Gerhard Vogel, editor; Springer-Verlag, New York, 2002; pp. 702-706).

Activity in an Osteoarthritis Model

Pain behavior was assessed by measurement of hind limb grip force (GF) in adult osteoarthritic rats. Male Sprague Dawley rats, 325-350 g, were injected in the unilateral knee join with a single intra-articular injection of sodium monoiodoacetate (MIA). All rats were tested at 20 days following MIA injection. A behavioral measure of activity-induced pain was carried out. Measurements of the peak hind limb grip force were conducted by recording the maximum compressive force ($CF_{max}$), in grams of force, exerted on a hind limb strain gauge setup, in a commercially available grip force measurement system (Columbus Instruments, Columbus, Ohio).

During testing, each rat was gently restrained by grasping it around its rib cage and then allowed to grasp the wire mesh frame attached to the strain gauge. The experimenter then moved the animal in a rostral-to-caudal direction until the grip was broken. Each rat was sequentially tested twice at approximately 2-3 min interval to obtain a raw mean grip force ($CF_{max}$). This raw mean grip force data was in turn converted to a maximum hindlimb cumulative compressive force ($CF_{max}$), as the grams of force/kg of body weight, for each animal.

For evaluating the compound effects, the hind limb grip force was conducted 20 days following the intra-articular injection of MIA. A group of age-matched naïve (not injected with MIA) animals was added as a comparator to the drug-dosed groups. The vehicle control response for each group of MIA-treated animals was defined as the 0% response (0% effect), whereas the naïve control group was defined as the normal response and as 100% effect. The % effects for each dose group was expressed as % return of response to normalcy, compared to the naïve group. That is, the % effect= (Treatment $CF_{max}$-Vehicle $CF_{max}$)/Vehicle $CF_{max}$]×100). Higher % effect numbers indicate increased relief from the pain in the model, with 100% indicating a return to the level of response seen in normal (non-osteoarthritic) animals. All experiments evaluating drug effects in this model were conducted in a randomized blinded fashion.

Animals, Compounds, and Dosing.

Male Sprague Dawley rats (250-300 g body weight) obtained from Charles River Laboratories (Wilmington, Mass.) were used for all experiments, unless indicated otherwise. The animals were housed in Association for Assessment and Accreditation of Laboratory Animal Care (AAALAC) approved facilities at Abbott Laboratories in a temperature-regulated environment under a controlled 12-h light-dark cycle, with lights on at 6:00 a.m. Food and water were available ad libitum at all times except during testing. All testing was done following procedures outlined in protocols approved by Abbott Laboratories' Institutional Animal Care and Use Committee.

The following table illustrating the efficacy in OA pain is provided, along with potency values:

| Compound Name (Example number) | dose injected, i.p. (intraperitoneally) | % Effect[1] |
|---|---|---|
| Example 1 | 1 mg/kg | 51 ± 6%** |
| Example 1 | 3 mg/kg | 79 ± 6%** |
| Example 2 | 3 mg/kg | 43 ± 13%* |
| Example 3 | 1 mg/kg | 26 ± 2%** |
| Example 3 | 3 mg/kg | 53 ± 5%** |
| Example 4 | 1 mg/kg | 40 ± 4%** |
| Example 4 | 3 mg/kg | 56 ± 6%** |
| Example 5 | 1 mg/kg | 54 ± 5%** |
| Example 5 | 3 mg/kg | 74 ± 4%** |
| Example 6 | 1 mg/kg | 65 ± 9%** |
| Example 6 | 3 mg/kg | 90 ± 17%** |
| Example 7 | 1 mg/kg | 51 ± 8%** |
| Example 7 | 3 mg/kg | 66 ± 6%** |
| Example 8 | 1 mg/kg | 47 ± 6%** |
| Example 8 | 3 mg/kg | 68 ± 4%** |
| Example 8 | 10 mg/kg | 82 ± 5%** |

[1]Data represent mean ± SEM.
Statistical significance *p < 0.05, **p < 0.01 as compared to vehicle-treated animals.
Note that celecoxib (30 mg/kg) is active as a positive control in this test, with a % Effect of 89% ± 5%**

Representative compounds are active in this model, with preferred compounds of the invention active in the model at doses of ranging about micromoles/kg of body weight.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A method of treatment of osteoarthritis pain comprising administration of a histamine $H_3$ receptor antagonist, a salt thereof, or a composition comprising such histamine $H_3$ receptor antagonist or salt, to a mammal in need of treatment thereof, wherein the histamine $H_3$ receptor antagonist is 2-[4-((1S,2S)-2-{[(2S)-2-methylpyrrolidin-1-yl]methyl}cyclopropyl)phenyl]pyridazin-3(2H) one.

2. The method of claim 1, wherein the histamine $H_3$ receptor antagonist is administered in a therapeutically effective amount with an effective amount of ibuprofen, celecoxib, or rofecoxib.

3. The method of claim 1, wherein the histamine $H_3$ receptor antagonist is administered in an amount of 0.001 to 30 mg/kg of body weight.

4. The method of claim 1, wherein the histamine $H_3$ receptor antagonist is administered in an amount of 1 mg/kg, 3 mg/kg or 10 mg/kg of body weight.

* * * * *